(12) United States Patent
Smith et al.

(10) Patent No.: US 11,986,310 B2
(45) Date of Patent: May 21, 2024

(54) OLFACTORY TEST SYSTEMS AND METHODS

(71) Applicant: Olfaxis, LLC, Durham, NC (US)

(72) Inventors: David William Smith, Durham, NC (US); Richard Michelli, Raleigh, NC (US); William D. Woolf, Durham, NC (US); Edward Karwacki, Garner, NC (US)

(73) Assignee: Olfaxis, LLC, Durham, NC (US)

( * ) Notice: Subject to any disclaimer, the term of this patent is extended or adjusted under 35 U.S.C. 154(b) by 924 days.

(21) Appl. No.: 16/648,046

(22) PCT Filed: Sep. 26, 2018

(86) PCT No.: PCT/US2018/052821
§ 371 (c)(1),
(2) Date: Mar. 17, 2020

(87) PCT Pub. No.: WO2019/067519
PCT Pub. Date: Apr. 4, 2019

(65) Prior Publication Data
US 2020/0253531 A1      Aug. 13, 2020

Related U.S. Application Data

(60) Provisional application No. 62/565,241, filed on Sep. 29, 2017.

(51) Int. Cl.
*A61B 5/00* (2006.01)
(52) U.S. Cl.
CPC .......... *A61B 5/4011* (2013.01); *A61B 5/0004* (2013.01); *A61B 5/4088* (2013.01);
(Continued)

(58) Field of Classification Search
None
See application file for complete search history.

(56) References Cited

U.S. PATENT DOCUMENTS

| 5,325,765 A | 7/1994 | Sylvan et al. |
| 5,840,189 A | 11/1998 | Sylvan et al. |

(Continued)

FOREIGN PATENT DOCUMENTS

| EP | 2174585 | 4/2010 |
| WO | 2006135368 | 12/2006 |

(Continued)

OTHER PUBLICATIONS

International Preliminary Report on Patentability of the International Searching Authority corresponding to International Patent Application No. PCT/US2018/052821 (7 pages) (dated Apr. 9, 2020).

(Continued)

*Primary Examiner* — Jay B Shah
(74) *Attorney, Agent, or Firm* — Myers Bigel, P.A.

(57) ABSTRACT

Methods, devices and systems for evaluating olfactory function are configured to: electronically estimate a user-specific odorant detection threshold sensitivity threshold using at least one target stimulus odorant delivered to a nose of a user; flowably deliver a plurality of different target stimulus odorants to the nose of the user with defined concentrations of the different target stimulus odorants based, at least in part, on the estimated user-specific odorant detection sensitivity threshold; and evaluate olfactory function of the user based on the user's response to the delivered different target stimulus odorants.

19 Claims, 23 Drawing Sheets

(52) U.S. Cl.
CPC .... *A61B 5/7275* (2013.01); *A61B 2560/0223* (2013.01); *A61B 2560/0252* (2013.01); *A61B 2560/0257* (2013.01); *A61B 2562/029* (2013.01)

(56) References Cited

U.S. PATENT DOCUMENTS

| | | | |
|---|---|---|---|
| 6,059,724 | A | 5/2000 | Campbell et al. |
| 6,325,475 | B1 | 12/2001 | Hayes et al. |
| 6,338,715 | B1 | 1/2002 | Hayes et al. |
| 6,557,394 | B2 | 5/2003 | Doty |
| 6,589,577 | B2 | 7/2003 | Lazaris et al. |
| 6,607,762 | B2 | 8/2003 | Lazaris et al. |
| 6,645,537 | B2 | 11/2003 | Sweeney et al. |
| 6,658,989 | B2 | 12/2003 | Sweeney et al. |
| 8,429,950 | B2 | 4/2013 | Wright |
| 8,469,293 | B2 | 6/2013 | Doty et al. |
| 8,820,265 | B2 | 9/2014 | Palmer et al. |
| 2006/0261179 | A1 | 11/2006 | Davies et al. |
| 2007/0077204 | A1 | 4/2007 | Devanand et al. |
| 2007/0186923 | A1 | 8/2007 | Poutiatine et al. |
| 2007/0295327 | A1 | 12/2007 | Bottomley |
| 2012/0018654 | A1 | 1/2012 | Wennberg et al. |
| 2013/0156897 | A1 | 6/2013 | Goldstein |
| 2013/0270176 | A1 | 10/2013 | Scheiber |
| 2014/0221269 | A1 | 8/2014 | Sobel et al. |
| 2015/0112161 | A1 | 4/2015 | Mills |
| 2016/0015309 | A1 | 1/2016 | Mills |
| 2016/0091470 | A1 | 3/2016 | Gafsou |
| 2016/0220165 | A1 | 8/2016 | Taherkhani et al. |
| 2016/0287161 | A1 | 10/2016 | Smith et al. |

FOREIGN PATENT DOCUMENTS

| | | |
|---|---|---|
| WO | 2010100567 | 9/2010 |
| WO | 2014154909 | 10/2014 |
| WO | 2016161261 | 10/2016 |

OTHER PUBLICATIONS

Yoder et al. "Characterizing Olfactory Binary Mixture Interactions in Fischer 344 Rats Using Behavioral Reaction Times" Chemical Senses, 40(5):325-334 (2015).
Laing et al. "Reaction time for the recognition of odor quality" Chemical Senses, 17(3):337-346 (1992).
Behrman et al. "Considering the senses in the diagnosis and management of dementia" Maturitas, 77(4):305-310 (2014).
Busek et al. "The influence of traumatic brain lesion on sleep architecture" Sbornik lekarsky, 101(3):233-239 (1999) (Abstract only).
Dixon et al. "A fluid percussion model of experimental brain injury in the rat" Journal of neurosurgery, 67(1):110-119 (1987).
Doty et al. "Odor perception in neurodegenerative diseases" Handbook of Olfaction and Gustation, Chapter 18, pp. 850-890 (2015) (Abstract only).
Doty, R.L. "Olfaction in Parkinson's disease and related disorders" Neurobiology of Disease, 46(3):527-552 (2012).
Lewine et al. "Quantitative EEG biomarkers for mild traumatic brain injury" Journal of Clinical Neurophysiology, 36(4):298-305 (2019).
Ling et al. "Mixed pathologies including chronic traumatic encephalopathy account for dementia in retired association football (soccer) players" Acta Neuropathologica, 133(3):337-352 (2017).
Nilsson et al. "Epileptic seizure activity in the acute phase following cortical impact trauma in rat" Brain Research, 637(1-2):227-232 (1994).
Rahayel et al. "The effect of Alzheimer's disease and Parkinson's disease on olfaction: a meta-analysis" Behavioural Brain Research, 231(1):60-74 (2012).
Ronne-Engstrom et al. "Continuous EEG monitoring in patients with traumatic brain injury reveals a high incidence of epileptiform activity" Acta Neurologica Scandinavica, 114(1):47-53 (2006).
Velayudhan et al. "Smell identification function as a severity and progression marker in Alzheimer's disease" International Psychogeriatrics, 25(07):1157-1166 (2013).
Walker A. E. "The physiological basis of concussion: 50 years later" Journal of Neurosurgery, 81(3):493-494 (1994).
Witkowski et al. "Rapid changes in synaptic strength after mild traumatic brain injury" Frontiers in Cellular Neuroscience, 13(166) (2019).
Doty et al. "Odor perception in neurodegenerative diseases" Handbook of Olfaction and Gustation. Chapter 23, pp. 850-890 (2003) (Abstract only).
Alaoui-Ismaili et al. "Odor Hedonics: Connection With Emotional Response Estimated by Autonomic Parameters" Chemical Senses, 22(3):237-248 (1997).
Alosco et al. "Olfactory Function and Associated Clinical Correlates in Former National Football League Players" Journal of Neurotrauma, 34:772-780 (2017).
Bakker et al. "Olfactory Dysfunction in Pediatric Traumatic Brain Injury: A Systematic Review" Journal of Neurotrauma, 31:308-314 (2014).
Bakker et al. "Recovery of Olfactory Function following Pediatric Traumatic Brain Injury: A Longitudinal Follow-Up" Journal of Neurotrauma, 33:777-783 (2016).
Bodyak et al. "Performance of Mice in an Automated Olfactometer: Odor Detection, Discrimination and Odor Memory" Chemical Senses, 24(6):637-645 (1999).
Cain et al. "Uniformity of Olfactory Loss in Aging" Annals of the New York Academy of Sciences, 561:29-38 (1989).
Callahan et al. "Assessment of Anosmia After Traumatic Brain Injury: Performance Characteristics of the University of Pennsylvania Smell Identification Test" Journal of Head Trauma Rehabilitation, 17(3):251-256 (2002).
Caminiti et al. "Detection of Olfactory Dysfunction Using Olfactory Event Related Potentials in Young Patients with Multiple Sclerosis" PLoS ONE, 9(7):e103151 (2014).
Coelho et al. "Posttraumatic olfactory dysfunction" Auris Nasus Larynx, 43:137-143 (2016).
De Guise et al. "Olfactory and executive dysfunctions following orbito-based lesions in traumatic brain injury" Brain Injury, 29(6):730-738 (2015).
Dhilla Albers et al. "Episodic Memory of Odors Stratifies Alzheimer Biomarkers in Normal Elderly" Annals of Neurology, 80(6):846-857 (2016).
Doty et al. "Presence of both odor identification and detection deficits in Alzheimer's disease" Brain Research Bulletin, 18(5):597-600 (1987) (Abstract only).
Doty et al. "A Study of the Test-retest Reliability of Ten Olfactory Tests" Chemical Senses, 20:645-656 (1995).
Drummond et al. "The Invisible Problem: The Incidence of Olfactory Impairment following Traumatic Brain Injury" Brain Impairment, 16(3):196-204 (2015).
Gudziol et al. "The impact and prospect of traumatic brain injury on olfactory function: a cross-sectional and prospective study" European Archives of Oto-Rhino-Laryngology, 271:1533-1540 (2014).
Hedner et al. "Cognitive factors in odor detection, odor discrimination, and odor identification tasks" Journal of Clinical and Experimental Neuropsychology, 32(10):1062-1067 (2010).
International Search Report and the Written Opinion of the International Searching Authority corresponding to International Patent Application No. PCT/US2018/052821 (10 pages) (dated Jan. 11, 2019).
Larsson et al. "Odor Identification in Old Age: Demographic, Sensory and Cognitive Correlates" Aging, Neuropsychology, and Cognition, 12(3):231-244 (2005).
Lötsch et al. "How Many and Which Odor Identification Items are Needed to Establish Normal Olfactory Function?" Chemical Senses, 41:339-344 (2016).
Lundstrom et al. "Methods for building an inexpensive computer-controlled olfactometer for temporally precise experiments" International Journal of Psychophysiology, 78(2):179-189 (2010).
Office Action issued for related U.S. Appl. No. 15/562,966 (14 pages) (dated Jan. 15, 2020).

(56) References Cited

OTHER PUBLICATIONS

Osborne-Crowley et al. "Hyposmia, Not Emotion Perception, is Associated With Psychosocial Outcome After Severe Traumatic Brain Injury" Neuropsychology, 30(7):820-829 (2016).

Ottaviano et al. "N-butanol olfactory threshold and nasal patency before and after palatal expansion in children. A preliminary study" International Journal of Pediatric Otorhinolaryngology, 78:1618-1623 (2014).

Patel et al. "Impaired olfactory discrimination learning and decreased olfactory sensitivity in aged C57BI/6 mice" Neurobiology of Aging, 30(5):829-837 (2009).

Ramalho et al. "Evolution of the perceived odour intensity assessed by GC-Olfactometry of emissions from household and building products" Poster presentation, CSTB Healthy Buildings 2006.

Ruff et al. "A Quantative Test for Olfaction is the Most Sensitive Physical Examination Biomarker for Residual Neurological Dysfunction Due to Mild Traumatic Brain Injury (mTBI) That can be Performed in the Setting of a Clinical Examination Room" Neurology, 80(7 Supplement) (5 pages) (2013).

SBIR-STTR Award to Osmic Enterprises, Inc. from the Department of Health and Human Services, Contract 4R44AG051311-02 (3 pages) (Awards year: 2016).

Schofield et al. "Traumatic brain injury and olfaction: a systematic review" Frontiers in Neurology, 5(5):1-22 (2014).

Sigurdardottir et al. "Olfactory Identification and Its Relationship to Executive Functions, Memory, and Disability One Year After Severe Traumatic Brain Injury" Neuropsychology, 30(1):98-108 (2016).

Tabert et al. "A 10-Item Smell Identification Scale Related to Risk for Alzheimer's Disease" Annals of Neurology, 58:155-160 (2005).

Xydakis et al. "Olfactory impairment and traumatic brain injury in blast-injured combat troops" Neurology, 84:1559-1567 (2015).

Yoder et al. "Evidence of rapid recovery from perceptual odor adaptation using a new stimulus paradigm" Attention, Perception, & Psychophysics, 76(4):1093-1105 (2014).

RT PLOT

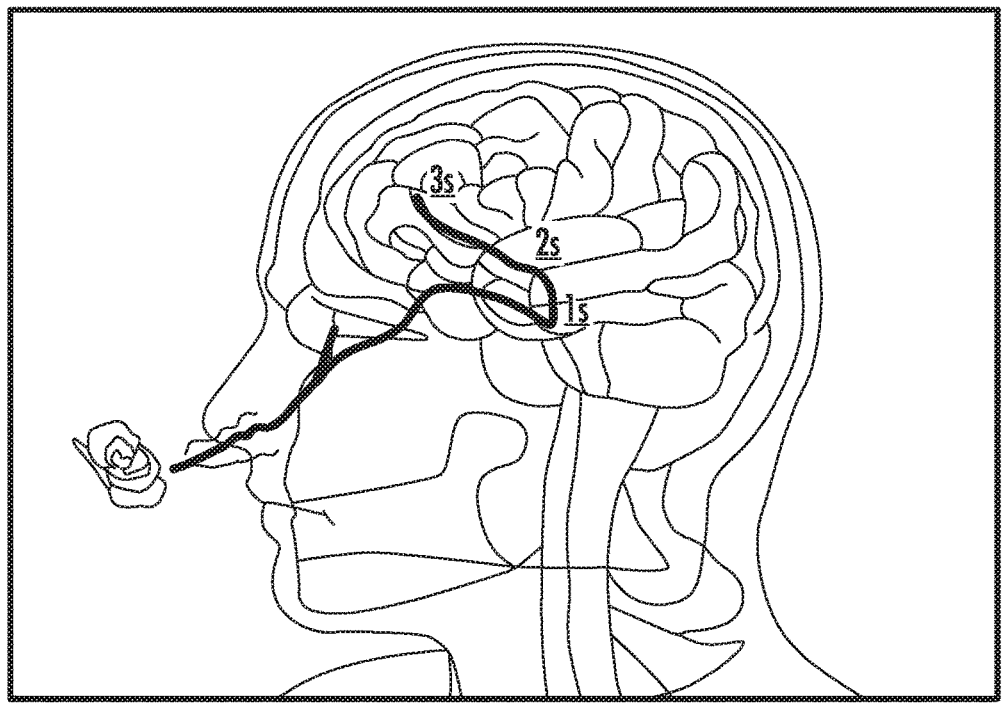
FIG. 5
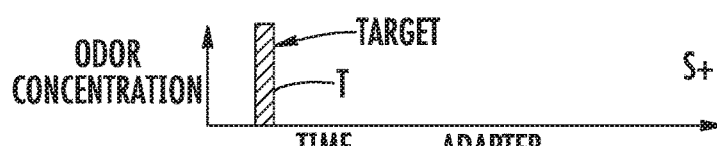
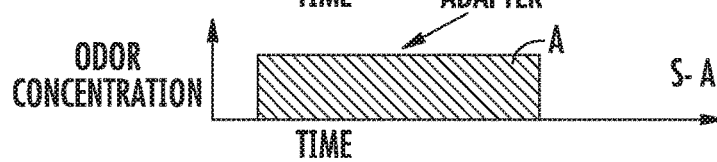
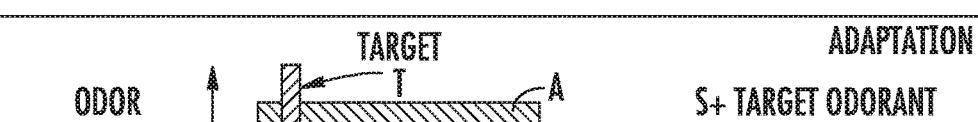
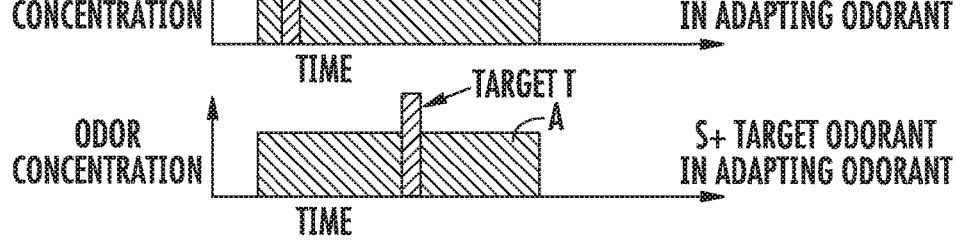

CONCEPTUAL MODEL AND STIMULUS PARADIGM TO MEASURE ADAPTATION

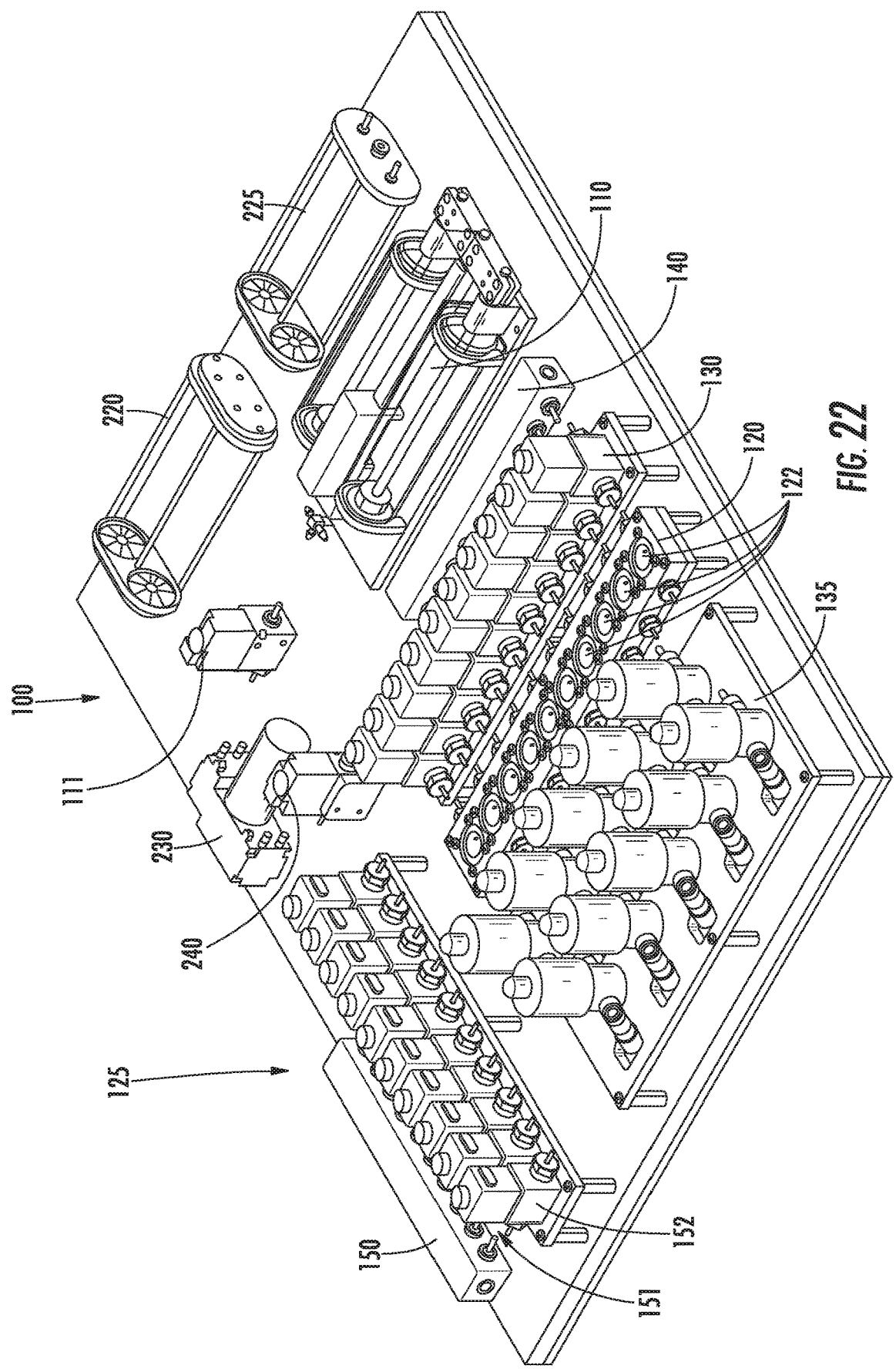

OLFACTORY TEST SYSTEMS AND METHODS

RELATED APPLICATIONS

This application claims the benefit of and priority to U.S. Provisional Application Ser. No. 62/565,241, filed Sep. 29, 2017, the contents of which are hereby incorporated by reference as if recited in full herein.

FIELD OF THE INVENTION

The present invention relates to devices and methods of evaluating olfactory function.

BACKGROUND OF THE INVENTION

Changes in olfactory function are known to be powerful indicators, or predictors, of neurological health. Current known olfactory function tests do not measure multiple aspects of olfactory function (e.g., odor threshold, odor identification, odor discrimination and odor adaptation), which reflect olfactory processes mediated at different levels within the brain. The University of Pennsylvania Smell Identification Test (UP SIT) and the SNIFFIN' STICKS test measure only odor identification and sensitivity measures, so they do not assess the functional status (damage) at multiple levels within the olfactory central nervous system. Moreover, no known existing commercial test of olfactory function provides for verification of the quality or concentration of the delivered odorant and/or user-specific detection threshold. One or both of these shortcomings, because decreases in olfactory function are biomarkers for debilitating neurodegenerative disease, can confound comparisons of repeated, longitudinal test results.

There remains a need for alternative olfactory testing systems.

SUMMARY OF EMBODIMENTS OF THE INVENTION

Embodiments of the invention are directed to methods, systems and devices that can evaluate olfactory function.

Embodiments of the invention can calculate a user-specific threshold sensitivity value.

The user-specific threshold sensitivity value can be compared to a baseline and a second later value to predict physiological changes in the CNS.

Olfactory function for tests such as, discrimination, odor ID and odor adaptation can be carried out using controlled, flowably delivered, target concentrations of different target stimulus odorants based, at least in part, on the estimated user-specific threshold sensitivity value.

Embodiments of the invention are directed to methods that: electronically estimate a user-specific odorant detection sensitivity threshold using at least one target stimulus odorant delivered to a nose of a user; flowably deliver a plurality of different target stimulus odorants to the nose of the user with defined concentrations of the different target stimulus odorants based, at least in part, on the estimated user-specific odorant detection sensitivity threshold; and evaluate olfactory function of the user based on the user's response to the delivered different target stimulus odorants.

The electronic estimate of the user-specific odorant detection threshold sensitivity threshold can include flowably delivering the at least one target stimulus odorant to the nose of the user in an ascending and/or descending staircase trial sequence and calculating a median or average of a concentration level associated with first and second positive identification concentration levels of different trials over time.

The method can include delivering a adapting odorant for a first duration and delivering one or more of the different target stimulus odorants concurrently with the adapting odorant and at an increased concentration relative to the adapting odorant and for a shorter duration than the adapting odorant to evaluate adaptation of the user.

The different target stimulus odorants can be flowably delivered to the nose of the user based on a nasal inhalation mask or nostril tube allowing one or more of: concurrent bilateral (birhinal) nostril delivery or independent monorhinal delivery.

The method can include delivering an adapting odorant for a first duration and delivering one or more of the different target stimulus odorants at different increasing onset intervals and shorter durations concurrently with the adapting odorant to evaluate adaptation of the user.

The method can include delivering an odorant for a first duration and delivering one or more (e.g., two) of the different target stimulus odorants at different increasing onset intervals and shorter durations to evaluate odor ID of the user.

The defined target stimulus odorants can be flowably provided in calibrated concentrations (ppm or ppb) that are adjusted to compensate for environment variables so that each target stimulus odorant is presented to the user in a precise reliable concentration (ppm or ppb) and/or is calculated post-delivery to identify a precise and reliable concentration (ppm or ppb) delivered to the user to thereby allow for standardization in measurements of olfactory function across different users similar to an eye chart for vision.

The flowably delivering can carried out in defined sequences, and the evaluating can measure four olfactory functions: sensitivity, odor identification, odor discrimination and odor adaptation.

The method can include electronically obtaining responses of the user and electronically transmitting the responses to a remote database for one or more of storage, reporting and analysis.

The method can include calculating an olfactory index based on the measured four olfactory functions.

The different target stimulus odorants that are flowably delivered to the user can include a series of homologous aliphatic alcoholics or aldehydes, sharing a common functional group, but varying from three to eight carbon atoms in length to test pairwise discrimination ability to thereby allow for testing of odor discrimination.

Odor ID can be tested using easily recognizable scents (rose, grass, gas, pine, chocolate and the like).

Threshold and adaptation can be tested using phenyl ethanol and/or butanol.

The defined concentrations can be calibrated concentrations that can be electronically adjusted according to local temperature, pressure and humidity conditions prior to, during or after the estimating and/or the flowably delivering.

The defined concentrations can be calibrated by providing fractional dilution values and saturation concentration for a respective target stimulus odorant at environmental local conditions, then converting the fractional dilution values to absolute values using the saturation concentration for the odorant.

The defined concentration values can be scaled concentration values calculated using the user-specific estimated sensitivity threshold.

The flowably delivering of the different target stimulus odorants can be carried out for: (i) discrimination testing of the user whereby the user is provided two different odorants to see if the user can detect whether they are different, (ii) adaptation testing whereby at least one adapting odorant is presented to the user with at least one of the target stimulus odorant and a response as to whether the target stimulus odorant is detected is obtained with or without an associated time of detection, and (iii) identification testing of the user whereby a response of the user to a correct identification of the target stimulus odorant delivered is measured. Each test may use different levels or odorant(s).

The flowably delivering of the different target stimulus odorants can include: providing the different target stimulus odorants in different odorant devices comprising sealed enclosed chambers in fluid communication with a fluid manifold; providing at least one syringe of a carrier gas in fluid communication with the manifold; flowing the carrier gas at a controlled flow rate from one of the at least one syringe through a first selected one of the sealed enclosed chambers to flow a respective associated target stimulus odorant in the enclosed chamber as an odorant vapor in the carrier gas into a flow path comprising the manifold then to a conduit attached to a nasal delivery device to deliver the target stimulus to the nose of the user.

The method can include purging the conduit, then flowing the carrier gas at a controlled flow rate from one of the at least one syringe through a second selected one of the sealed enclosed chambers to flow a respective associated target stimulus odorant as an odorant vapor in the carrier gas into a flow path comprising the manifold then to a conduit attached to the nasal delivery device, which can optionally be a mask, for monorhinal or birhinal delivery.

The at least one syringe can be coupled to a three-way valve that selectively coupled the at least one syringe to either a clean air input or the fluid manifold.

The method can include electronically controlling the controlled flow rate of the carrier gas based on a target concentration value of a selected target stimulus odorant, a saturation concentration for the first selected odorant, and a target concentration relative to the saturation concentration.

The method can include adjusting the controlled flow rate from one of the at least one syringe through the first selected one of the sealed enclosed chambers based on local environmental conditions.

Other embodiments are directed to methods of evaluating olfactory function by: delivering different target stimulus odorants to a user, the different target stimulus odorants varying from three to eight carbon atoms in length; and testing pairwise discrimination ability of the user based on whether the user can detect a difference in odor between the delivered different target stimulus odorants.

Still other embodiments are directed to methods of evaluating olfactory function, by calculating an olfactory index (Olfaxis Index; "OI") by combining measurements of sensitivity of odor identification, odor discrimination, odor adaptation and odor detection thereby allowing a standardized parameter that permits direct comparison of individual retests and a demographically relevant population.

The calculation is carried out by one of:

$$OI = a \cdot \text{Detection} + b \cdot \text{Discrimination} + c \cdot \text{Identification} + d \cdot \text{Adaption},\quad\quad 1)$$

wherein Detection, Discrimination, Identification, and Adaptation are a test subject's score on a specific functional test, which may be raw or normalized for a population. The a, b c, and d parameters are scale factors of defined numerical values;

$$OI = \text{Detection}^w + \text{Discrimination}^x + \text{Identification}^y + \text{Adaptation}^z \quad\quad 2)$$

Detection, Discrimination, Identification, and Adaptation are the test subject's score on a specific functional test, which values may be raw or normalized for a population, and the exponents w, x, y, and z are defined numerical values; or $$OI = a \cdot \text{Detection}^w + b \cdot \text{Discrimination}^x + c \cdot \text{Identification}^y + d \cdot \text{Adaptation}^z \quad\quad 3)$$

Detection, Discrimination, Identification, and Adaptation are a test subject's score on a specific functional test, which may be raw or normalized for a population, and the a, b, c, and d factors are scale factors and w, x, y, and z are exponents, and each scale factor and exponent are defined numerical values.

The CH is a standardized score range, such as 0-1, 0-10 or 0-100, with lower or higher ranges associated with increased risk of neurological impairment or disorder.

Still other embodiments are directed to olfactory test systems that include: a housing: a fluid manifold in the housing comprising an input distributor and an output distributor; a plurality of odorant source devices comprising different target stimulus odorants in fluid communication with the fluid manifold in the housing; a plurality of valves coupled to the sealed enclosed chambers and the fluid manifold; a carrier gas supply in fluid communication with the fluid manifold and the odorant source devices; and a controller coupled to the valves and configured to direct selected ones of the valves to open and provide at least one open active flow path that comprises a first active flow path segment through the input distributor and one or more of the odorant source devices, and a second active open flow path segment through the output distributor. The first and second active flow path segments merge into a common exit flow path downstream of the output manifold and downstream of the odorant devices whereby an odorant gas mixture of odorant and carrier gas from a respective open active flow path is delivered to a user.

The controller can be configured to estimate a user-specific threshold sensitivity value and calculate target concentrations of the different target stimulus odorants based, at least in part, on the estimated user-specific threshold sensitivity value.

The system can include a wireless module in the housing coupled to or defining the controller.

The carrier gas supply can include at least one syringe coupled to an actuator and the controller can be configured to control the actuator to adjust a desired flow rate of the carrier gas through the at least one active open flow path.

The controller can be configured to direct the actuator to depress the syringe plunger in a manner that adjusts the flow rate of the carrier gas based on a target concentration value of a selected target stimulus odorant, a saturation concentration for the first selected odorant, and a target concentration relative to the saturation concentration.

The controller can be configured to adjust a flow rate of the carrier gas supply through the at least one open active flow path based on local environmental conditions.

The system can include a three-way valve coupled to each respective at least syringe. The three-way valve can selectively and serially connect the respective syringe to the input manifold or a clean air source, and the respective syringe retracts when connected to the clean air source and dispenses the clean air as a carrier gas when connected to the input manifold.

The odorant source devices can be provided as a modular unitary cartridge body that is detachable from the housing and replaceable with another modular unitary cartridge body to thereby allow different sets of odorants or replacement of the same odorants.

The system can have 6-12 different sealed enclosed chambers of different odorants held side-by-side as the odorant devices.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

These and other objects and/or aspects of the present invention are explained in detail in the specification set forth below.

BRIEF DESCRIPTION OF THE DRAWINGS

FIG. 5 is a prophetic image of the use of odor presentation to identifier presentation visual delay (shown, by way of example as 1 s, 2 s, 3 s) to increase cognitive load and/or testing function at different neural locations in the brain according to embodiments of the present invention.

FIGS. 6A-6D are graphs of odor concentration versus time illustrating an odor adaptation stimulus protocol according to embodiments of the present invention. FIG. 6A illustrates odor concentration of a target odorant delivered to a subject alone. FIG. 6B illustrates an adapting odorant delivered to a subject alone. FIG. 6C and FIG. 6D illustrate graphs of an adaption delivery of a target odorant with an adapting odorant.

FIG. 22 is a perspective view of the system shown in FIG. 21.

DETAILED DESCRIPTION

Figure 1A:
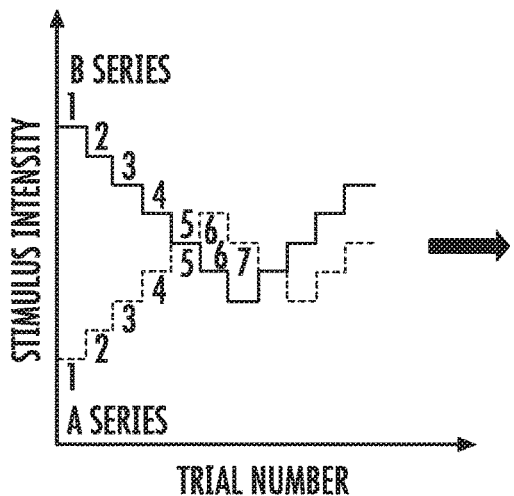
FIG. 1A and FIG. 1B are graphs of stimulus intensity versus trial number of exemplary odorant delivery sequences of ascending and/or descending stimulus intensity that can be used to establish a user-specific threshold of sensitivity according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. The term "Fig." (whether in all capital letters or not) is used interchangeably with the word "Figure" as an abbreviation thereof in the specification and drawings. In addition, the sequence of operations (or steps) is not limited to the order presented in the claims unless specifically indicated otherwise.

The term "concurrently" means that the operations are carried out substantially simultaneously.

The term "about" means that the noted value can vary by +/−20%.

It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected to the other element or intervening elements may be present. In contrast, when a feature or element is referred to as being "directly connected", "directly attached" or "directly coupled" to another element, there are no intervening elements present. The phrase "in communication with" refers to direct and indirect communication. Although described or shown with respect to one embodiment, the features so described or shown can apply to other embodiments.

The term "circuit" refers to software embodiments or embodiments combining software and hardware aspects, features and/or components, including, for example, at least one processor and software associated therewith embedded therein and/or executable by and/or one or more Application Specific Integrated Circuits (ASICs), for programmatically directing and/or performing certain described actions, operations or method steps. The circuit can reside in one location or multiple locations, it may be integrated into one component or may be distributed, e.g., it may reside entirely or partially in a portable housing, a workstation, a computer, a pervasive computing device such as a smartphone, laptop or electronic notebook, or partially or totally in a remote location away from a local computer or processor of a respective test unit or device or a pervasive computing device such as a smartphone, laptop or electronic notebook. If the latter, a local computer and/or processor can communicate over local area networks (LAN), wide area networks (WAN) and can include a private intranet and/or the public Internet (also known as the World Wide Web or "the web" or "the Internet"). The test system can comprise appropriate firewalls for HIPPA or other regulatory compliance. In the traditional model of computing, both data and software are typically substantially or fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers. Test protocols and/or data obtained by various test systems can use the Cloud.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

In the description of embodiments of the present invention that follows, certain terms are employed to refer to the positional relationship of certain structures relative to other structures. As used herein, the term "front" or "forward" and derivatives thereof refer to the general or primary direction that the filler or product travels in a production line to form an encased product; this term is intended to be synonymous with the term "downstream," which is often used in manufacturing or material flow environments to indicate that certain material traveling or being acted upon is farther along in that process than other material. Conversely, the terms "rearward" and "upstream" and derivatives thereof refer to the directions opposite, respectively, the forward and downstream directions.

Generally stated, embodiments of the present invention provide olfactory test systems 10 (FIGS. 2A-2D, for example) and methods that can "standardize" the measurement of human olfactory function.

Calibrated stimuli: odorant presentations or deliveries to respective patients/users can be flowably provided in known concentrations (ppm or ppb) which can be adjusted to compensate for environment and odorant variables so that every odorant stimulus is presented to a user in a precise reliable concentration (ppm or ppb) or can be calculated post-delivery to identify a precise and reliable ppm/ppb as used in the test. The term "calibrated" means that the delivered concentration of respective stimuli odorant mixtures has an accuracy and/or precision of at least +/−7% mean error or better, more typically at least +/−5% or better, and may correspond to between 1 and 2 ppm at a low or lowest concentration (below 1/64 dilution) and between 5 and 15 ppm at a highest concentration.

Standard test protocols and/or paradigms: the test system 10 can ensure that odorant stimuli are presented in the exact same sequence and timing for every test or for every test protocol.

Measures the four olfactory functions: the system 10 can deliver calibrated odorant stimuli in sequences and combinations to measure sensitivity, odor identification, odor discrimination and odor adaptation.

Intelligent measure of higher level olfactory functions: the system 10 can measure sensitivity/threshold and adjusts (scales) odorant stimuli for subsequent odorant identification (oID), odorant discrimination and odorant adaptation tests based on the sensitivity of that subject to standardize the measure of higher level olfactory functions.

Automated capture of subject responses: test subject responses can be electronically captured locally and transmitted to a remote database for reporting and analysis.

Verifiably repeatable and transferable results across multiple tests, subjects, and devices.

Embodiments of the invention can provide olfactory function tests that have clinical utility and may be used for patient screening, i.e. to deliver results that inform decisions about treatment of patients, potentially in conjunction with other testing. Standard measurements can be captured in a reportable database will over time provide data for research to establish olfactory degradation due to aging and understand and differentiate normal olfactory decline from pathological degradation, or decline due to neurological disorder (ND)—disease or injury. It is contemplated that standard measures of olfactory function can quantify "normal" (similar to an eye chart for assessing vision, e.g., like 20/20 for vision) and may lead to drug development, clinical trials, and/or research on medicines and therapies to treat the specific ND.

Embodiments of the invention can use evaluation of olfactory function to assess whether a patient/user may have Traumatic Brain Injury (TBI). While there are some differences, degradation of olfactory function can also be a biomarker for other neurological conditions and diseases.

Olfactory neural pathways, originating in the nasal cavity, reach into the central nervous system where they branch diffusely within the brain; these tracts play critical roles in the brain's most important functions, including emotion, memory and executive function. As a consequence, damage to any of these areas can result in changes in cognitive, emotional and olfactory function (cf., Osborne-Crowley, 2016; Alosco et al., 2016). Research studies have repeatedly shown a relationship between olfactory dysfunction and TBI (Frasnelli et al., 2015; Caminiti et al., 2013; Drummond et al., 2015). The contents of these documents are hereby incorporated by reference as if recited in full herein. TBI is one of the most common causes of olfactory dysfunction, though most of the afflicted are unaware of the sensory deficit.

Increasing evidence suggests that olfactory dysfunction may serve as a potential marker of structural and functional neural damage associated with brain injury events. Studies suggest the degree of olfactory loss is proportional to the severity of brain injury and that changes in olfaction may indicate the locus of insult (cf., Bakker et al., 2014; Coehlo and Costanzo 2016; Callahan et al., 2002; Gudziol et al., 2014; Schofield et al., 2014; Sigurdardottir et al., 2016). Olfactory deficits can be observed in TBI cases where radiographic imaging failed to identify lesions (Caminiti et al., 2013; Xydakis et al., 2015). The contents of these documents are hereby incorporated by reference as if recited in full herein.

There are significant differences in findings across studies, reflecting both the complexity of the brain, but, just as importantly, inadequate olfactory measures, a lack of standardization and diverse behavioral methodologies (Ruff et al., 2013; Schofield et al., 2014; Xydakis et al., 2015; Lotsch et al., 2016; de Guise et al., 2015). The contents of these documents are hereby incorporated by reference as if recited in full herein.

It is believed that (surprisingly) to date, there has been no systematic comparison of the sensitivity and specificity of the different olfactory measures (e.g., changes in odor sensitivity or odor identification) in characterizing the type, location and magnitude of brain injury.

The rapidly growing literature linking changes in olfactory function to brain trauma suggests that olfactory dysfunction may be an effective, immediate and non-invasive tool for identifying subtle neural alterations for early identification of both TBI severity and localization (Ruff, 2013). To be effective biomarkers, and because the olfactory tracts innervate and play a role processing in many diverse cortical regions, it may be important to develop and utilize different, standardized olfactory measures to effectively characterize the location and magnitude of TBI within the brain. For instance, odor sensitivity (threshold measures) impacts the main olfactory epithelium, while odor discrimination deficits typically indicate changes to the olfactory bulb. Odor adaptation, however, is known to affect two distinct areas: the main olfactory epithelium and the piriform cortex, whereas odor identification reflects higher order changes, typically within the piriform and prefrontal cortices. Consistent with these associations, odor identification deficits have also been shown to occur with injuries to different locations on the head (de Guise et al., 2015; Lotsch et al., 2016; Xydakis et al, 2015), particularly with frontal lobe head strikes (Bakker et al., 2014). The contents of these documents are hereby incorporated by reference as if recited in full herein.

To be effective, predictors of TBI-induced neurologic insult based on olfactory measures are preferably standardized to permit direct comparisons both of individual test-retest and individual results against a demographically-appropriate population (Ruff 2013; Ruff et al., 2014). The contents of these documents are hereby incorporated by reference as if recited in full herein.

Two known existing olfactory tests, developed in the 1980s and 1990s, are a pencil and paper scratch-and-sniff test for odor identification, and a magic marker-like pen sniff test to measure olfactory sensitivity. Neither of these relatively rudimentary tests employ specified, calibrated test stimuli, in an automated test paradigm using standardized odorant concentrations delivered to the subject nor transmits test results to a dynamic, demographic database, nor is there any verification of what is actually delivered to a subject. These conventional tests do not assess individual variations in sensitivity, or control for environment variables at the test site, and lack the sensitivity, specificity and repeatability believed important to serve as diagnostic tools for patients.

Also, current known olfactory function tests do not measure multiple aspects of olfactory function (e.g., odor threshold, odor identification, odor discrimination and odor adaptation), which reflect olfactory processes mediated at different levels within the brain. The University of Pennsylvania Smell Identification Test (UPSIT) measures only odor identification and the SNIFFIN' STICKS test measure only odor identification and sensitivity measures, so they do not assess the functional status (damage) at multiple (all) levels within the olfactory central nervous system. Additionally, odor identification depends on both executive brain function and verbal memory abilities, which can confound interpretation of test findings. Given that memory networks are often markedly impaired following head trauma, (particularly in moderate to severe cases) this restriction can diminish their diagnostic capability.

Embodiments of the invention can provide one or more standardized tests of the four distinct olfactory domains for screening and categorizing brain injury patients. It is contemplated that a demographic population database can be generated for different olfactory measures for providing improved olfactory behavioral measures from an individual suffering a TBI, allowing a comparison across patients, institutions and studies. Having a comprehensive database of longitudinal olfactory results of a subject and/or across a population, may offer a potentially powerful tool to guide community medical policy. Finally, because olfactory measures are economically feasible, noninvasive, and easy to administer, they may allow for quicker identification of TBI patients and screenings (including real time or near real time evaluations of athletes at athletic events/sites), as well as identify potential olfactory phenotypes for evaluating degrees of impairment.

Embodiments of the invention can provide a "standardized" measure of smell that provides calibrated/specified odorant concentrations with a test protocol providing a timing of odorant delivery that can be the same in each and every corresponding test between users and between test units. Slight variations in odorant delivery timing can alter sensitivity (through the process of odor adaptation) and, in doing so, may throw off test-retest reliability (test sensitivity).

Exemplary Test Sequence
1. Test training; present high level odorant to familiarize; train breathing (i.e., 1-3 seconds exhale, 1-3 seconds inhale—odorant presented during inhale; present one or several "training" single odorant trials.
2. Estimate a user-specific odorant detection sensitivity threshold (typically using a combined ascending/descending staircase procedure).
3. Use the threshold estimate to adjust an odorant concentration on subsequent tests, such that all subsequent tests can be conducted at the same concentration relative to sensitivity, including odor discrimination, and odor adaptation, so that some or all of the different odorant testing is performed at the same level relative to the user/patient's estimated threshold. As is discussed below, this is in contrast to known current olfactory tests. Indeed all other known devices present test odorants at the same, fixed odorant concentration, regardless of user/patient sensitivity. This means that using all other devices/technologies, the test odorants are presented to someone who is hypersensitive and to someone who is functionally incapable of smelling [an anosmic] are presented at the same level, making direct comparisons very difficult and confusing changes in sensitivity with changes in other measures, such as odor identification.

Estimating Threshold

Like all sensory systems, the olfactory sensitivity declines with age; odor detection threshold increases with age. Odor detection (threshold) is conceived of as being a sensory process, likely reflecting the initial transduction and encoding of the odorant within the sensory epithelium. It has been suggested that most common age-related changes in olfaction are the result of age-related changes in other, independent systems that, in turn, affect olfactory function.

Using an "Intelligent" Odorant Concentration Adjustment

Degradations in detection sensitivity (i.e., increases in threshold) would also be reflected as impairments in processing at higher levels within the olfactory CNS. In other words, decreases in low level olfactory sensitivity would likely cause decreases in OID performance, independent of higher level cognitive dysfunction indicative of AD or PD. To separate changes in sensitivity due to normal aging, from higher level cognitive changes that are evident in OID, we will adjust the level of test odorants to an estimate of threshold taken during that test session.

In all known current tests and technologies, including most laboratories, odorants are presented to test subjects at the same concentration. The problem with this is that no two people have the same overall olfactory sensitivity.

The most widely used test of olfactory function in the world is the scratch-and-sniff University of Pennsylvania smell identification test (UPSIT). Now imagine administering the same scratch and sniff test to two otherwise normal people, one who was normosmic (had a normal, sensitive sense of smell) and the second who was had bad allergies, and was having a great deal of difficulty smelling things. The normosmic person would likely, identify all of the odors correctly, while the other person with the allergies might misidentify a number of the odors.

If, however, the OID odorants are presented at a much higher concentration to the patient with allergies, and they could detect the odors as well as the normosmic person, they might score equally well on the OID test. Using this approach, the OID odorant concentrations are different for the two subjects, but are at the same level relative to threshold. The two patient's thresholds simply differ.

Embodiments of the invention provide a test device with a test protocol designed to first estimate a patient's detection threshold, then intelligently adjust the level (concentration) of odorants used in other test protocols to the same concentration relative to threshold.

Methods to Estimate User Olfactory Discrimination Sensitivity Threshold

In order to distinguish normal, age-related changes in olfactory sensitivity from high-level, neurodegenerative disease related cognitive dysfunction, embodiments of the invention can employ a staircase procedure to estimate a user/patient detection sensitivity threshold. In some embodiments, an average or median threshold estimate can be generated from at least one of an ascending or descending concentration series which can be used as a calculated user-specific sensitivity threshold estimate to adjust target odorant concentration values for a test sequence composed of one or more olfactory test of odor discrimination, odor identification and/or odor adaptation for that user.

Figure 1B:
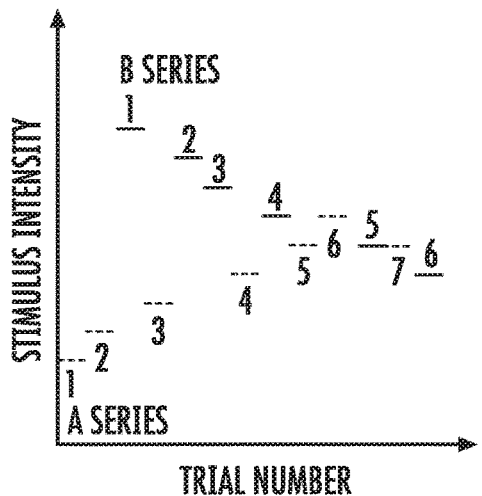

FIG. 1A and FIG. 1B illustrate a combined ascending/descending staircase psychophysical procedure. Stimulus level from trial-to-trial can be systematically increased or decreased, based on whether or not the subject detected the odorant. In a descending series (illustrated as "B series"), the initial odorant concentration is set well above threshold, then decreased on following trials following correct detection. Likewise, it is increased on subsequent trials when the subject fails to detect odorant presentation. For an ascending series ("A series"), the odorant level is initially set well below threshold, and is increased on subsequent trials when the subject fails to report detection. The series can be presented in order (all descending first, then ascending) per FIG. 1A or intermixed (optionally randomly) per FIG. 1B.

Figure 1C:
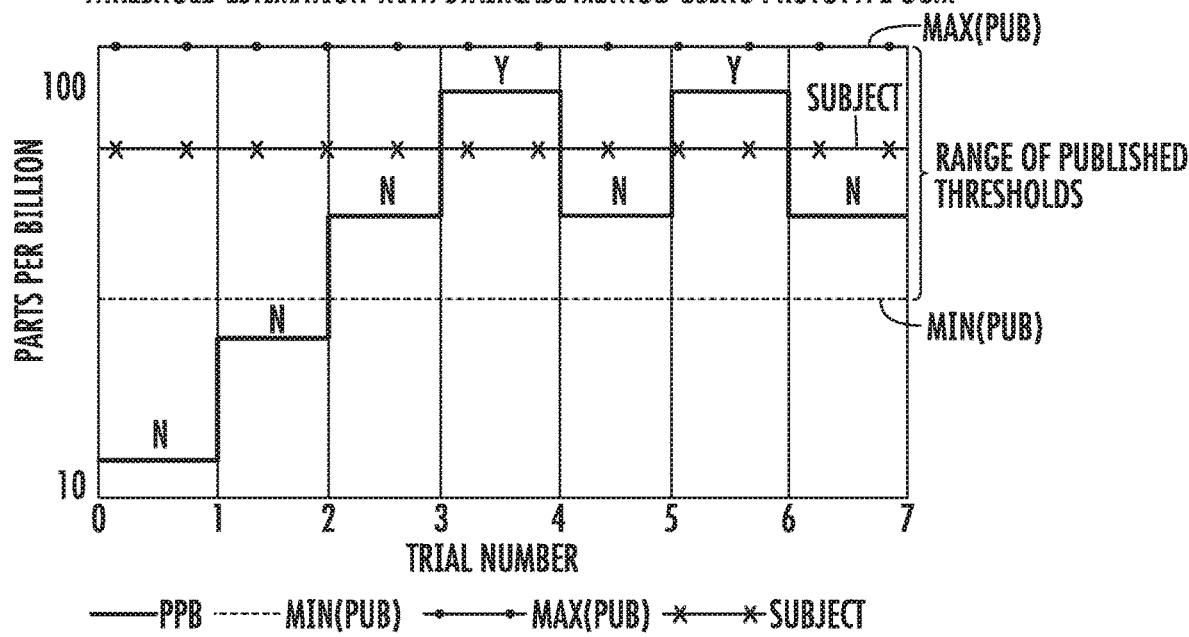
FIG. 1C is an example graph of parts per billion (ppb) per trial number of a staircase sequence for threshold estimation according to embodiments of the present invention.
Figure 2A:
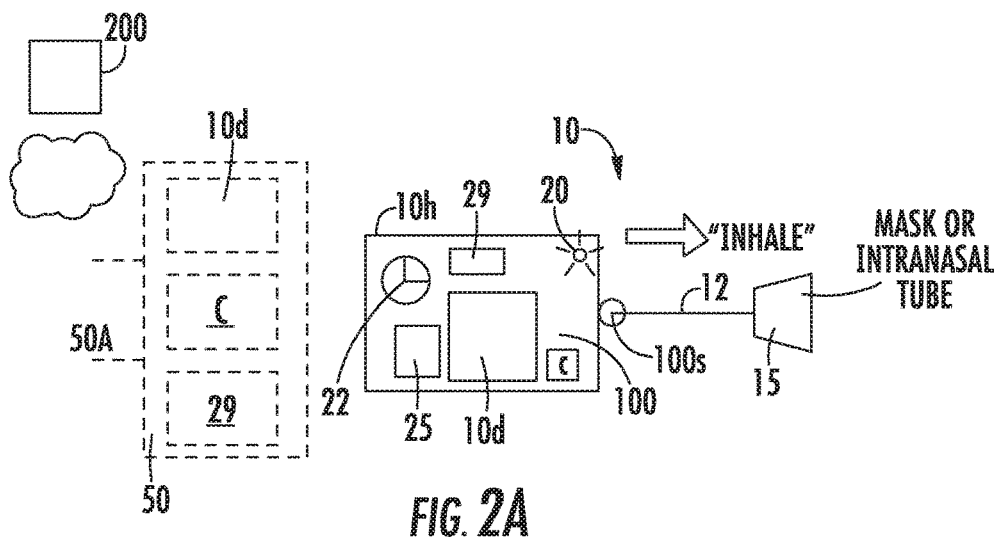
FIG. 2A is a schematic illustration of an example olfactory test system according to embodiments of the present invention.
Figure 2B:
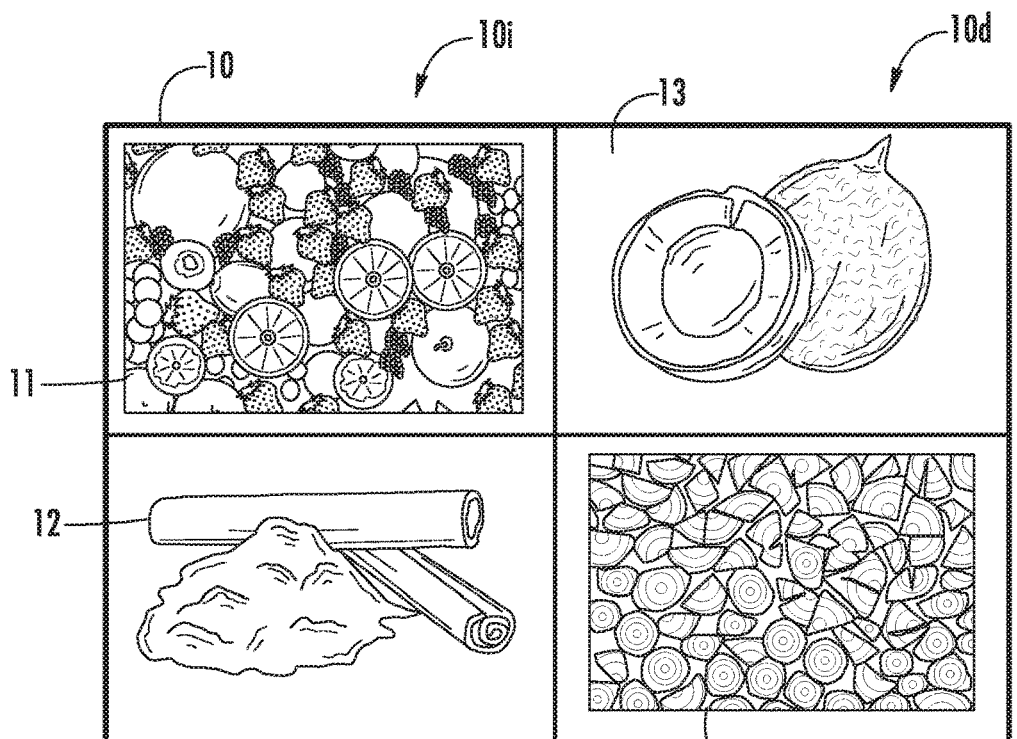
FIG. 2B is a schematic illustration of an example visual display of different items associated with different odors that can be provided on a display associated with or coupled to the olfactory test system according to embodiments of the present invention.

FIG. 1C illustrates a staircase sequence that can be used to deliver a target odorant to a user to estimate a user sensitivity threshold. A target odorant, such as, by way of example, a 1:2 dilution of citral in mineral oil (3 ppm saturation) can be delivered through a conduit 12 (i.e., TEFLON®, glass or stainless steel tube or other suitable inert material flow delivery device) to a nasal delivery device 15 (FIG. 2A). The odorant can be presented in an ascending concentration from a low level, i.e., 12 ppb (1/256), and increased a controlled amount, such as by doubling in concentration, for each trial until detection is reported by the user, whereupon, the concentration can be decreased until the user fails to report detection of the presence of the odorant. The example shown in this graph indicates a threshold of 70 ppb for this user which is with the published range of 28-120 ppb. Thus, when testing an individual, it is possible to adjust delivered/presented concentrations of stimuli odorant's based on the results of a threshold test and this can be described as measuring olfactory function with an "intelligent" (adaptive) procedure. Taking this approach allows subsequent olfactory tests to be performed at the same level relative to that subject's threshold. For example, if a person is hyposmic and has high thresholds for the detection of odorants, an "intelligent" approach can adaptively adjust (increase) the odorant levels for use in measuring odor identification and/or odor discrimination.

Figure 23A:
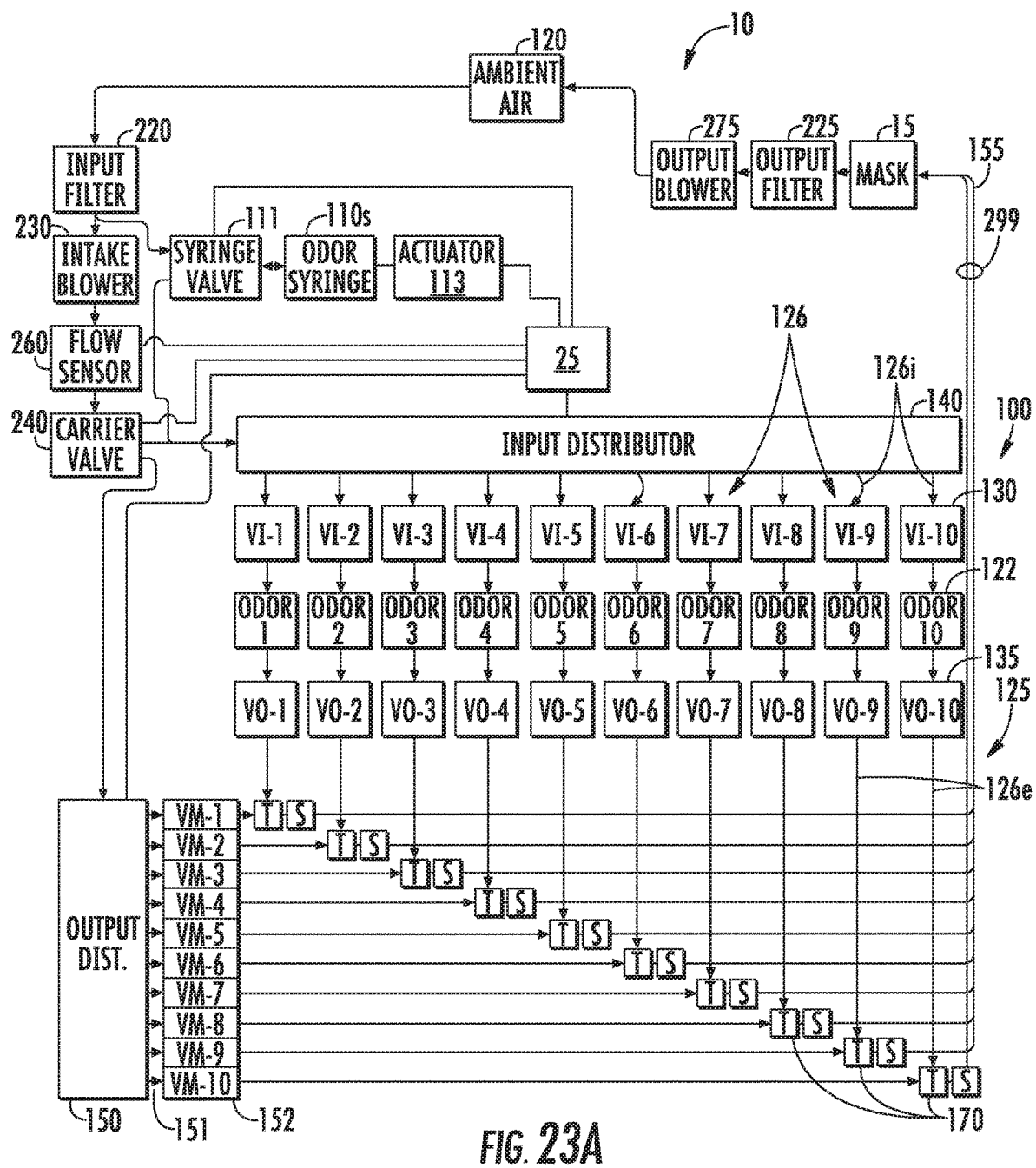
FIG. 23A is a schematic view of the system shown in FIGS. 21 and 22.
Figure 23B:
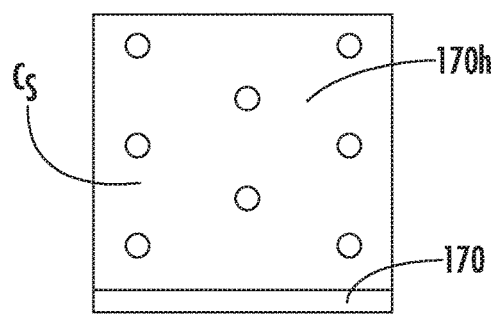
FIG. 23B is a schematic illustration of a headspace that can contain a saturated concentration of odorant according to embodiments of the present invention.

One way to normalize and/or adjust the level of test odorants used in subsequent testing relative to a user specific threshold follows. This adjustment can be calculated in several ways. One example is: Prior to testing, determine relative concentration for each odorant as a ratio of nominal detection level vs. saturation (i.e., 5 ppm/20 ppm=0.025 detection/saturation). The term "saturation" means the maximum concentration of odorant generated in gas (such as air) produced by aerosolization in a segment of an odorant generation path. For example, saturation can occur at the maximum concentration of an odorant that has been dissolved into a headspace 170h coupled to an ultrasonic transducer 170 (FIG. 23B). In some embodiments, a saturation concentration Cs of an odorant in the headspace in fluid communication with a delivery flow path 126 (FIG. 23A) can be provided using an ultrasonic transducer that creates a mist when a liquid phase odorant is exposed to or dropped onto the ultrasonic transducer.

Once the threshold test determines the test subject's threshold, the test subject's relative threshold can be determined by dividing his/her threshold by the nominal threshold (1 ppm/0.5 ppm=2), meaning this test subject requires concentrations at least 2× of nominal for detection. Subsequent identification concentrations can be scaled by this correction factor.

In some embodiments, the threshold can be estimated using relative concentrations vs. absolute. For example, if a nominal threshold corresponds to $1/128^{th}$ dilution and a test subject's threshold is identified as $1/32^{nd}$ dilution, the test system can use 1/128/1/32=4 as a correction factor for target odorant stimuli concentrations.

If an otherwise perfectly healthy human has a head cold or sinus infection, for example, the threshold for detecting a scent of a rose or other odorant stimulus can increase so that it can be much harder to smell the rose or other odorant stimulus, so their detection threshold can increase. As such, it can take a much higher concentration of rose or other odorant stimulus to be detected by smell. While there are no changes in higher-level olfactory or neural function, the change in sensitivity within the nasal cavity can alter other measures of smell (e.g., odor discrimination, odor identification, odor adaptation).

Embodiments of the invention provide at least one defined sensitivity odorant. The at least one defined sensitivity odorant can include butanol and/or phenyl ethyl alcohol. In some embodiments, both butanol and phenyl ethyl alcohol can be serially dispensed and used to calculate a user-specific sensitivity threshold. Carbon dioxide may serve as an odorant to test sensitivity of the trigeminal nerve (CN5), and as a comparison for odorants that primarily stimulate the olfactory nerve (CN1), such as vanillin.

Some researchers have discussed a potential relationship between changes in lower level sensitivity (i.e., increases in threshold) and resulting changes or effects on higher-level olfactory function, but it is not believed that anyone has actually measured this. See, e.g., Cain, W. S. and Stevens, J. C., 1989. Uniformity of Olfactory Loss in Aging. Annals of the New York Academy of Sciences, 561: 29-38. doi: 10.1111/j.1749-6632.1989.tb20967.x; Doty, R. L., McKeown, D. A., Lee, W. W. and Shaman, P., 1995. A study of the test-retest reliability of ten olfactory tests. *Chemical senses,* 20(6), pp. 645-656; Doty, R. L., Reyes, P. F. and Gregor, T., 1987. Presence of both odor identification and detection deficits in Alzheimer's disease. Brain research bulletin, 18(5), pp. 597-600; Hedner, M., Larsson, M., Arnold, N., Zucco, G. M. and Hummel, T. 2010. Cognitive factors in odor detection, odor discrimination, and odor identification tasks, Journal of Clinical and Experimental Neuropsychology, 32:10, 1062-1067, DOI: 10.1080/13803391003683070; and Larsson, M., Öberg, C. and Bäckman, L., 2005. Odor identification in old age: Demographic, sensory and cognitive correlates. Aging, Neuropsychology, and Cognition, 12(3), pp. 231-244. The contents of these documents are hereby incorporated by reference as if recited in full herein.
Relative Vs. Absolute Threshold Without measuring saturation concentration, and without compensating for temperature, pressure, and humidity, in some embodiments, the threshold test can be performed using half-dilution steps to determine a relative threshold (i.e. $1/64^{th}$ saturation). Current values of temperature, pressure, and humidity can be measured and electronically stored for later conversion of concentrations from relative to absolute.
Intelligent Odor Identification The most widely used tool for assessing olfactory status is the odor identification test (OID), though its format varies substantially from test to test (e.g., scratch and sniff, test pens, or squeeze bottles). Odor identification tasks are considered higher-level cognitive measures because of the necessary odor familiarity/memory and language ability. The ubiquitous finding, regardless of manufacturer, mode of odor presentation, and the number and choice of odorants employed, is an age-dependent decline in odor identification ability; the ability to identify simple odorants decreases with age.

Declines in olfactory sensitivity are a hallmark of the normal aging process. It is contemplated that embodiments of the invention can address these complications by adapting odorant concentrations used in testing, as described above, and present all odorants at the same level relative to threshold.

Furthermore, declines in olfactory function, including but not limited to odor sensitivity and OID can be evaluated in longitudinal testing of respective subjects, such as in annual or regular "well visit" medical screenings and Pre-participation Physical Exams for sports, similar to blood pressure measurements and the like.

Odorants

Figure 2C:
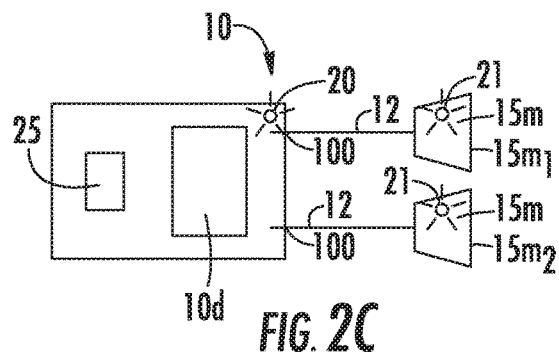
FIG. 2C is a schematic illustration of another example of an example olfactory test system according to embodiments of the present invention.
Figure 2D:
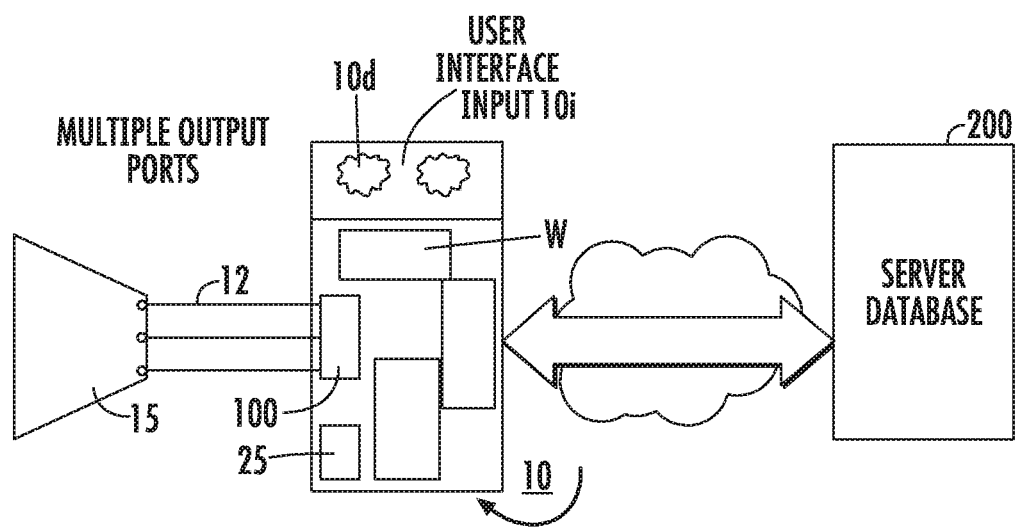
FIG. 2D is a schematic illustration of another example olfactory test system according to embodiments of the present invention.

Depending upon the odor identification test or test protocol, between six (6) and forty (40) odorants can be presented. Recent research has shown that not all odorants equally contribute to identifying neurodegenerative diseases, and has suggested that many fewer odorants, perhaps as few as six might be equally effective. Embodiments of the invention contemplate using a plurality of individual successive target odorants or concurrent combinations of odorants, for certain test protocols, typically between 4-12, such as 10. Examples of target stimuli odorants include odorants such as, but not limited to, menthol, clove, leather, strawberry, pineapple, smoke, soap, natural gas, lemon, cinnamon, turpentine, lemon, smoke, chocolate, rose, paint thinner, banana, pineapple, gasoline, soap, and/or onion. As one of skill in the art will appreciate; one or more organic and/or inorganic compounds may provide and/or contribute to a certain odorant. For example, the smell associated with an odorant may be provided by one or more organic and/or inorganic compounds. Example organic compounds that may be associated with and/or contribute to an odorant include, but are not limited to, damascenone (e.g., beta-damascenone), 3-methylbutanal, vanillin, phenyl ethyl alcohol, 3-methylcyclopentadecanone, geraniol, ethyl 2-methoxybenzoate, and/or 2-pinene. Example inorganic compounds that may be associated with and/or contribute to an odorant include, but are not limited to, hydrogen sulfide, carbon dioxide, and/or ammonia Example Testing Tasks As shown in FIGS. 2A, 2C, and 2D, typically after a trial run and/or after training the patient to inhale/exhale on command, a test device 10 with a housing 10h and with at least one controller 25 can direct an odorant gas delivery system 100 to flowably provide a defined concentration of a target odorant stimulus, optionally a high level odorant, to a nasal delivery device 15 for a suitable inhalation period, such as in a range of 0.5-3 seconds per target odorant stimuli. The nasal delivery device 15 can comprise a mask or intra-nasal tube. The nasal delivery device 15 can be configured for either or both concurrent bilateral (birhinal) nostril delivery or independent monorhinal delivery.

An audio and/or visual output 20 can indicate a user command (i.e., instruction) to "inhale" that can be output to the user/patient concurrent with the flowable delivery of the odorant gas stimuli. This audio and/or visual output or instruction can be an alarm, readable information on a video screen, an LED light and/or a spoken instruction to "inhale". The device 10 may also include an "exhale" audio and/or visual output by the speaker, video screen or other output device 20. The test device 10 may also include an onboard or remote timer 22 for timing delivery of the target stimuli gas T, an adapting odorant A and/or measuring identification response time, for example.

The housing 10h can be portable, ruggedized and light weight for ease of field use.

In some embodiments, the controller 25 can communicate with a flow sensor 100s in the delivery flow path of the odorant gas delivery system 100 can be used to automatically synch initiation of a delivery flow of target odorant gas to a user.

With delivery or after a variable interval (possibly including a simple cognitive task, like answering an unrelated question " . . . what day of the week is it?") at least one image (FIG. 2B) containing objects lists, or pictures of possible odorant descriptors 11-14, with or without word labels, or only word lists, can be presented as a physical document and/or provided by a display 10d which can be a touchscreen display. The user/patient can identify (such as touch on a touchscreen of a display) an image from the presented images 11, 12, 13, 14 that best identifies what they smell or smelled. The user-response of identification can be physical, verbal and/or electronic.

The test device 10 can include a user interface 10i such as one or more of a touch screen, an electronic mouse, cursor, or configured to accept speech responses or other inputs that allows a user to select the identified object associated with the odorant. The test device 10 can include an environmental sensor module 29 that can provide local pressure, humidity and temperature data.

As shown in FIG. 2A, the display 10d may be onboard the test device 10 that provides the odorant stimuli to the delivery device 15. Optionally, the display 10d and/or environmental sensor module 20 may be provided by a smartphone, electronic notebook, tablet computer, or other separate device 50 (shown in broken line) that can be wirelessly or hard-wired coupled to the olfactory test device 10.

For smartphone or notebook access, the test protocol can be provided by an APP 50A that can communicate with the test device 10 and that can send test data to a remote database and/or server 200. The term "APP" refers to software functionality provided by a computer program typically accessible via an icon.

A camera C in communication with the test device 10 may also be used to accept the user's identification of the odorant. The camera C, where used, can be onboard the test device 10 and/or implemented using a camera C of a remote device 50 such as a smartphone or electronic tablet or notebook that can be in communication with the test device 10.

FIG. 2C illustrates that the test device 10 can be configured to accommodate a plurality of nasal delivery devices 15 such as inhalation masks 15m with a gas delivery system 100 that can serially direct gas flow into a desired one of the conduits 12 and one of the corresponding different inhalation masks 15.

FIG. 2D illustrates that the test device 10 can communicate with a remove server database 200 for transmitting patient test data. The test device 10 can include a wireless module W. The term "wireless module" refers to a device, such as a microchip package, that has a wireless transceiver with a processor and optionally a plurality of general purpose input and output ports. The wireless module can support at least one of: a) standard single input, single output (SISO) wireless data transfer or b) a (high capacity) multiple input, multiple output (MIMO) wireless data transfer, WIFI or LTEVO chip, for example.

Figure 2E:
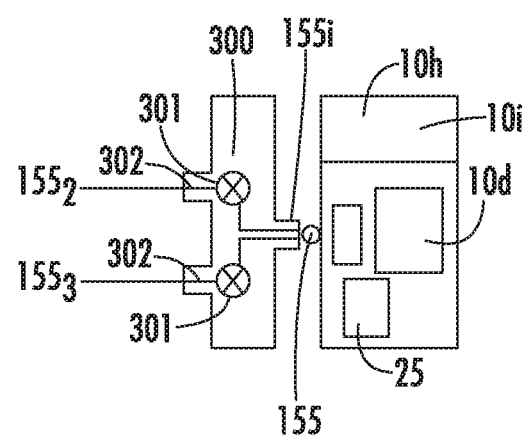
FIG. 2E is a schematic illustration of another example olfactory test system according to embodiments of the present invention.

FIG. 2E illustrates that the test system 10 may direct all odorant outputs to a single output port 155. A plug-on external module 300 can provide a multi-port $155_2$, $155_3$ capability. The plug-on external module 300 can couples to the housing 10h of the test device. For example, a single onboard port 155 can connect to the output module 300, which contains valves 301 and manifold plumbing with flow paths 302 to direct the single port flow 155i to one of 2 or 3 other output ports $155_2$, $155_3$, as directed by the controller 25.

Intelligent Odor Discrimination (iOD; Carbon-Chain Discrimination).

A series of homologous aliphatic alcoholics or aldehydes, sharing the same functional group, but varying from three to eight carbon atoms in length, can be used to test pairwise discrimination ability (i.e., the ability to discriminate on basis of a different number of carbon atoms). Performance on pairwise discriminations is, normally, an orderly function of relative difference in the number of carbon atoms between the two odorants presented. For example, if two alcohols (or two aldehydes) differ only by one carbon atom, the discrimination is difficult, but gets easier with a greater (2-carbon, 3-carbon, etc) difference. With olfactory impairment, the more degraded, the greater the number of carbon atoms required to make discrimination.

Example Test Odorants

Alcohols: 1-propanol, 1-butanol, 1-pentanol, 1-hexanol, 1-heptanol, 1-octanol.

Aldehydes: n-butanal, n-pentanal, n-hexanal, n-pentanal, n-octanol, n-nonanal,

Task

Different carbon discrimination test protocols are possible. In some embodiments, two odorants having the same functional group (i.e., both being alcohols or aldehydes), but varying in number of carbon atoms, can be presented in sequence through same nasal mask 15 (FIG. 2A), and the subject can be prompted or asked if they are different. In some embodiments, two odorants having the same functional group (i.e., both being alcohols or aldehydes), but varying in number of carbon atoms, can be presented in sequence through two different nasal masks $15_1$, $15_2$ (FIG. 2C), and the subject is asked if they are different. In some embodiments, three odorants having the same functional group (all being alcohols or aldehydes), but varying in number of carbon atoms (two odorants delivered are the same, the third is different), are presented in sequence through same nasal mask, or three different masks, and the subject is asked if to identify the DIFFERENT odorant. The concentration can be set relative to threshold for the patient and is not required to be fixed patient to patient or test to test. Where multiple devices 15 are used, such as multiple nasal masks, each mask $15m_1$, $15m_2$ may have an audio or visual output 21 that indicates it is "live" or the one that is to be used for that inhalation test sequence.

Metric

The more structurally similar two odorants are that can be discriminated, the more sensitive; the greater the structural difference necessary to be discriminated, the more impaired. In other words, a very sensitive nose can distinguish the difference between two odorants that differ by only one carbon atom, while an insensitive nose, or a person suffering from a neurodegenerative disease, may require a difference of four or more carbon atoms.

Carbon chain discrimination can be performed by delivering a particular functional group, say aldehydes or alcohols, then having the subject attempt to discriminate different chemicals in that class that vary only in the number of carbon atoms they contain. Table 1 below provides examples of chemicals.

TABLE 1

Discrimination Pairs and Carbon Differentials

| Discrimination pairs | Carbon length | Δ Carbons |
|---|---|---|
| Butanol-Propanol | 4 C vs. 3 C | 1 |
| Pentanol-Butanol | 5 C vs. 4 C | 1 |
| Hexanol-Pentanol | 6 C vs. 5 C | 1 |
| Heptanol-Hexanol | 7 C vs. 6 C | 1 |
| Octanol-Heptanol | 8 C vs. 7 C | 1 |
| Propanol-Pentanol | 3 C vs. 5 C | 2 |
| Butanol-Hexanol | 4 C vs. 6 C | 2 |
| Pentanol-Heptanol | 5 C vs. 7 C | 2 |
| Hexanol-Octanol | 6 C vs. 8 C | 2 |
| Hexanol-Propanol | 6 C vs. 3 C | 3 |
| Heptanol-Butanol | 7 C vs. 4 C | 3 |
| Octanol-Pentanol | 8 C vs. 5 C | 3 |
| Propanol-Heptanol | 3 C vs. 7 C | 4 |
| Butanol-Octanol | 4 C vs. 8 C | 4 |
| Octanol-Propanol | 8 C vs. 3 C | 5 |

An olfactory carbon discrimination paradigm can create a continuum of discrimination abilities, akin to an ever decreasing letter "E" on a Snellen eye chart. With the letter "E" continuum, the test is to identify the smallest "E" that can be visually identified. With carbon chain discrimination, the test goal is to identify the smallest difference (i.e., the fewest number of carbon atoms separating the two odorants) in carbon atoms that can be discriminated via smell by a user/patient. Using the top example in Table 1, butanol and propanol differ by one carbon atom (butanol has four, propanol has three) and they smell very much alike. As a result, olfactory discrimination is very difficult for most people. However, discriminating propanol and octagonal (octagonal has eight and propanol has three) is relatively simple because the smells are dissimilar.

It is believed that a continuum olfactory discrimination test can be a powerful tool for assessing small changes in olfactory function in either case of TBI or neurodegenerative diseases, for example. That is, it is not a simple yes or no between discrimination of two odorants as the test system can (gradually) increase or decrease the number of carbon atoms differing between the two and make the odorants more different to obtain a finer granular response as to the user/patient's discrimination ability.

Reaction Time

Figure 3:
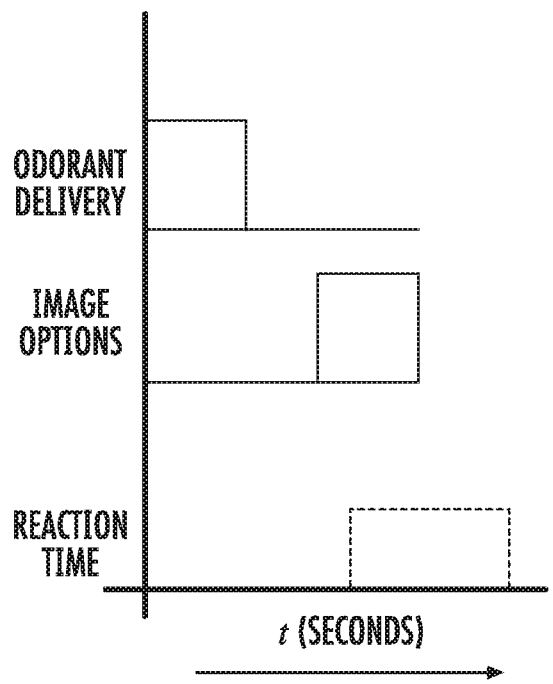
FIG. 3 is an exemplary timing diagram of different testing actions (seconds) that can be used to assess olfactory function according to embodiments of the present invention.

The speed of information processing and decision-making can be estimated by measuring behavioral reaction time (RT). Significant increases in RT, reflect a slower decision speed, can be used as an indicator of several conditions such as depression, dementia, schizophrenia, and cognitive aging. Reaction time can be automatically measured by the test unit 10 between presentation of either the odorant and the patient's decision/identification of the odorant picture and/or descriptor, or between the presentation of the picture and/or descriptor and subsequent identification of the perceived odor. FIG. 3 illustrates an example of a timing diagram for evaluating reaction time.

By way of discussion, a simple way to understand the use of RT is by example of accidentally touching a hot stove. Imagine using the stove to warm up some food and you accidentally placing your hand on the burner. If the burner has just been turned off, you will barely get your hand on it and you'll pull it away very quickly—the reaction time is very fast, near zero. Under the same conditions, except for the fact that the burner was turned off one minute ago, you place your hand on the same burner. This time is nearly as fast, but it had slower reaction time because you have to set your hand all the way on the burner before you realize it's very hot because it has started to cool. Let's say RT is one second. Now, let's say the burner had been turned off for three minutes. In this case, you put your hand on the burner and you can leave it there for 2 seconds before it gets uncomfortable and you lift your hand off. Next time you there is a 5-minute delay and your RT to remove your hand is now 10 seconds and, after 10 minutes, you can leave your hand on for 20 seconds. So, as the pain related to the heat is reduced, it is less "salient", reaction time goes up—RT, in this example, is a predictor of the level of pain (and is related to the temperature of the burner).

By way of analogy in the realm of olfactory function, in the pain example above, the temperature of the heat stimulus varied with measured RT. Substituting this action with exposure to varying defined concentrations of a single odorant, reaction time can vary in a similar fashion. At high concentration levels (equivalent to high temperatures above), odorant is very salient and a reaction time to report detection of the stimulus should be very brief. As concentration of the odorant is decreased, or the sensitivity of the nose has degraded, it might (it will . . . ) take longer and longer to report detection. In this manner, increases in RT over time (e.g., over years) for the same odorant can indicate decreases in olfactory sensitivity for that user.

Figure 4:
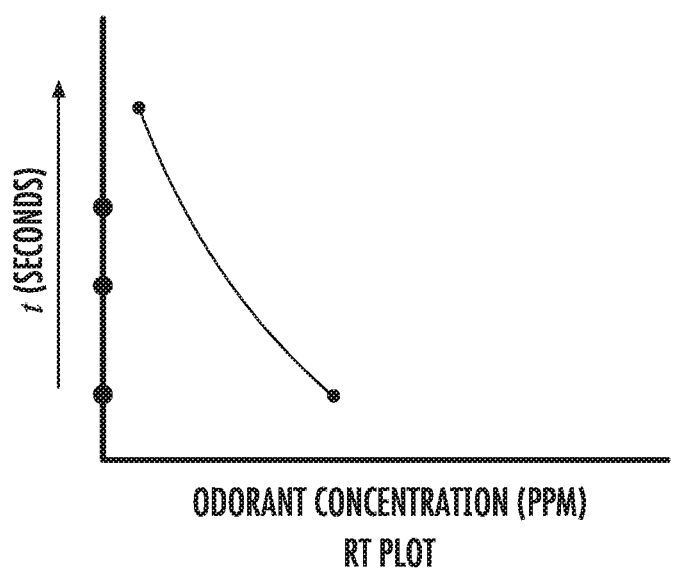
FIG. 4 is a graph of time (seconds) versus odorant concentration (ppm) that can be used to evaluate a subject's olfactory function by measuring behavior reaction time (RT) according to embodiments of the present invention.

Thus, a difference between simply asking a patient if they detect an odor or not is a "yes" or "no" answer, nothing else. By adding an RT measure to the test, an indication of "salience" can be obtained by, for example, looking at a slope of an RT plot such as shown in FIG. 4; the steeper the function the faster the perception that the stimulus is changing.

It is contemplated that measuring RT in an OID task can be a helpful parameter. Imagine if, after smelling an odor, a user/patient can identify the correct descriptor after one second, versus a longer time period, such as 30 seconds to correctly the identical odorant on a different day. In both cases, the user/patient got the answer correct, as the correct descriptor for that odorant was identified, but the second day it took a lot longer. In this case, whether the answer was "yes" or "no" does not reveal the differences in processing on the two days. By adding RT, however, the test can have an entirely different answer or a further parameter for evaluation.

Reaction Time References: Laing, D. G. and MacLeod, P., 1992. Reaction time for the recognition of odor quality. Chemical Senses, 17(3), pp. 337-346; Yoder, W. M., Gaynor, L., Windham, E., Lyman, M., Munizza, O., Setlow, B., Bizon, J. L. and Smith, D. W., 2015. Characterizing Olfactory Binary Mixture Interactions in Fischer 344 Rats Using Behavioral Reaction Times. Chemical senses, p.bjv014. The contents of these references are hereby incorporated by reference as if recited in full herein.

Cognitive Load

A recent study by Albers et al., 2016 (see reference, below) has demonstrated the power of varying cognitive load on identifying Alzheimer's patients, or the conversion from mild cognitive impairment (MCI) to full-blown Alzheimer's. In the classical UPSIT test (and the like), the person scratches an odor and patch on the same page as a list of descriptors. In this test, the patient only has to recognize the name.

The OID odorant can be provided to the user/patient, then the patient is asked to identify the odorant. The interval between presentation of the odorant and presentation of the response display with images on a screen showing possible descriptors (pictures and/or words) can be varied. During some tests, the patient can be asked a simple, but unrelated question (what day of the week is it?, what is your name?, etc. . . . ), with the objective being to manipulate the temporal processing of the odor memory, which occurs at different levels within the olfactory central nervous system (CNS). The initial processing of the odor memory might occur in one area of the brain, whereas seconds later the processing might be occurring at higher levels. By doing these simple manipulations, the functional status at different areas within the CNS can be evaluated.

FIG. 5 is a schematic of a hypothetical depiction of use of odor presentation to identifier presentation delay. When using the standard UPSIT test, the patient scratches on the odor patch, and the list of identifier alternatives ("grass", "leather", "rose", "soap") is immediately adjacent to the patch. So the patient sees the list of descriptors while they are scratching and sniffing on the patch.

In some embodiments of the present invention, the patient can smell/inhale the odorant, and the test system 10, i.e., display 10d can wait one or more delay periods before presenting the images or list of descriptors (or pictures of descriptors). By doing that, the test system 10 is increasing cognitive load (requiring them to remember for longer and longer periods of time) and allowing for odor processing at different levels within the central nervous system and, theoretically, testing the function at those areas.

In this hypothetical depiction of that paradigm, the solid line from the nose to the brain shows the path of the odor neural signal as it leaves the rose and goes up through the olfactory sensory neural system. With the one second delay (1 s), the odor signal can reach and the odor may be testing what's going on in the anterior piriform cortex; with a two second delay (2 s), the odor signal might reach and the odor may be evaluating what's going on in the posterior piriform cortex; with a three second delay (3 s), the odor signal can be evaluating what's going on in the prefrontal cortex. See, e.g., Dhilla Albers, A., Asafu-Adjei, J., Delaney, M. K., Kelly, K. E., Gomez-Isla, T., Blacker, D., Johnson, K. A., Sperling, R. A., Hyman, B. T., Betensky, R. A. and Hastings, L., 2016. Episodic memory of odors stratifies Alzheimer biomarkers in normal elderly. *Annals of neurology*, 80(6), pp. 846-857. The contents of which are hereby incorporated by reference as if recited in full herein.

Odor Adaptation

Following determination of threshold for the target odorant, the adapting odorant concentration for each participant is set at some level (i.e., twice) their threshold concentration. Setting the adapting stimulus level in this manner, whereas the absolute concentration of the adapting stimulus varies across patients, or over time for the same patient, may ensure that the relative level is consistent over time for an individual and across participants.

Figure 7:
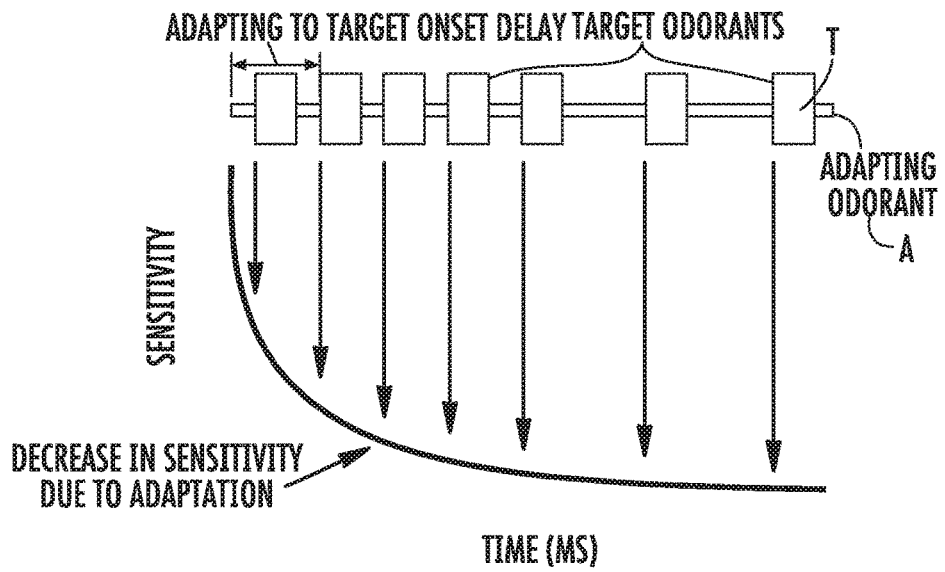
FIG. 7 is a graph of sensitivity versus time (ms) of a that can be used to assess and/or measure odor adaptation based on delivery of long adapting odorant to brief target odorants where a time course of odor adaptation can be measured by estimated changes in threshold for brief odorants presented at different adapting odorant onset to target odorant onset delays according to embodiments of the present invention.

Examples of stimulus conditions employed in estimating a time course of adaptation are shown in FIGS. 6A-6D. The effect of adaptation can be estimated as a change in olfactory sensitivity (i.e., a change in threshold) produced by a "simultaneous" longer (i.e., 1500-ms) adapting or "adapting" odorant M. To estimate the adaptation time course, target stimulus odorant "T" thresholds are estimated for different adapting-to-target stimulus onset delays, ranging from 50 to 900 ms. Adaptation can be very rapid (~100 ms). Embodiments of the invention are only interested in determining if there is adaptation, so the normal target stimulus T threshold (with no adapting odorant; top line FIG. 6A) can be compared to the estimated threshold in the presence of the adapting odorant A with a first delay in FIG. 6C and/or a longer second delay (i.e., a 300 ms onset delay) in FIG. 6D. FIG. 7 illustrates a conceptual model and stimulus paradigm to measure adaptation. Not all onset delays need be used or measured based on the model shown in FIG. 7.

The odorant threshold can be first estimated for the target odorant alone (top line, FIG. 6A; also see odor threshold discussed above). An adapting odorant (FIG. 6B) can be set relative to some fixed level or to the estimated threshold (i.e., twice the estimated threshold). Adaptation is then estimated as the increase in detection sensitivity threshold for the same odorant measured in the presence of the adapting odorant. The adapting odorant is chemically different and different in concentration. See, Yoder et al., Evidence of rapid recovery from perceptual odor adaptation using a new stimulus paradigm, Atten Percept Psychophys, 6 Feb. 2014, the contents of which are hereby incorporated by reference as if recited in full herein.

The sensitivity contour shown in FIG. 7 illustrates a theoretical (and measured) decrease in olfactory sensitivity produced by odor adaptation during presentation of a long duration odorant (horizontal line, top). The time course of odor adaptation can be measured by estimated changes in threshold sensitivity over time (ms) for brief odorants presented at different adapting odorant onset to target odorant onset delays (see also, FIGS. 6C, 6D).

Olfaxis Index

Figure 8:
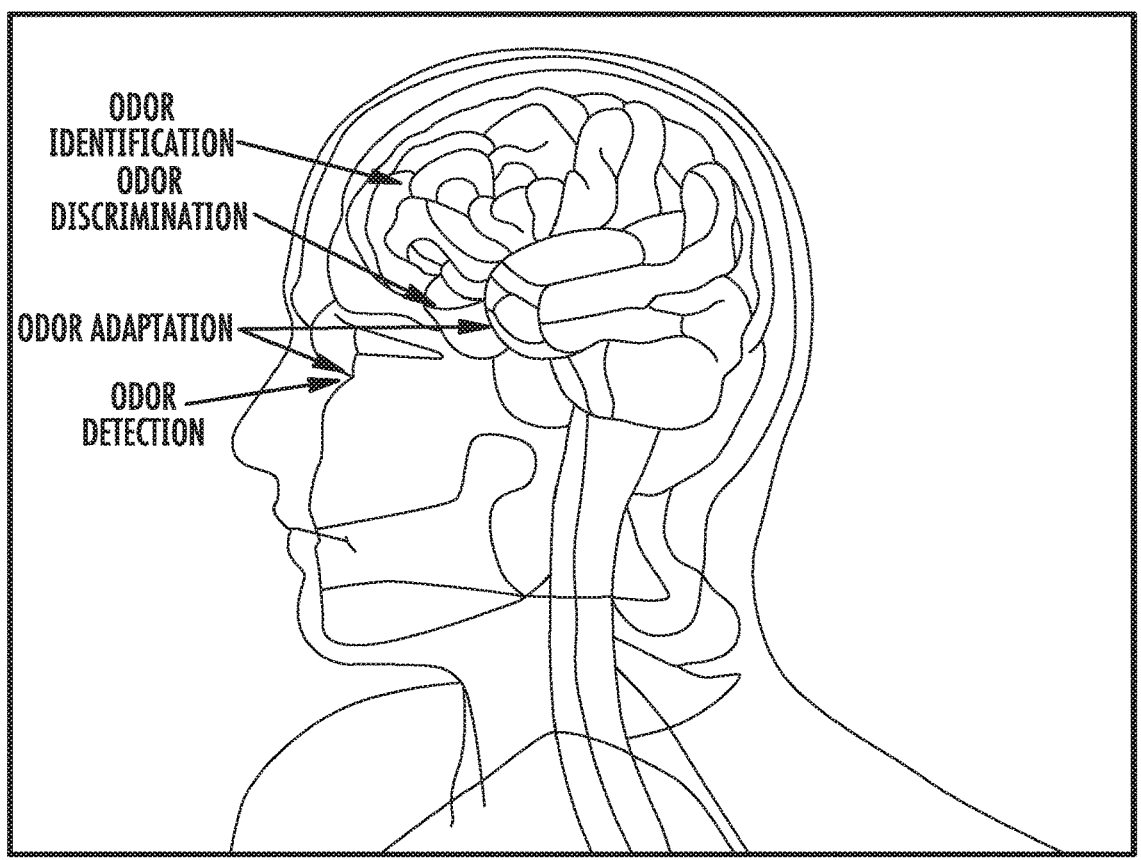
FIG. 8 is a simplified schematic illustration of a human brain illustrating four different olfactory parameters (Odor Identification, Odor Discrimination, Odor Adaptation and Odor Detection) that can be evaluated using the olfactory test systems and methods of embodiments of the present invention.

Referring to a simplified depiction in FIG. 8, each level in the olfactory central nervous system (CNS) is involved in a different aspect in odor processing (technically speaking one may not be able to detect an odorant without the rest of your brain beyond the olfactory epithelium). The lowest level of odor processing, odor detection is performed by olfactory sensory neurons in the olfactory epithelium within the nasal cavity. The ability to discriminate between odorants (odor discrimination) is accomplished in the olfactory bulb. The ability to name, or identify an odor (odor identification) is a higher level, cognitive function that occurs between the posterior piriform cortex and the prefrontal cortex.

Changes in neural function in any of these brain regions results in alterations in the associated olfactory function, and can be quantified by olfactory testing. For example, changes in sensitivity can quantify changes in neural density within the main olfactory epithelium, and degradations in odor discrimination can reveal pathophysiological changes in the olfactory bulb.

It is believed that there is good scientific evidence to suggest that by combining all measures of olfactory function (detection, discrimination, identification and adaptation) that a comprehensive olfactory "index" (FIG. 9) can be calculated and used to identify pathological changes in one or more brain region, which might be indicative of a neurodegenerative disease or brain trauma.

Some olfactory measures can be more directly related to underlying neurological disorders than others. A weighting function, which emphasizes more accurate measures, and down plays others, might be used to optimize the index.

Figure 9:
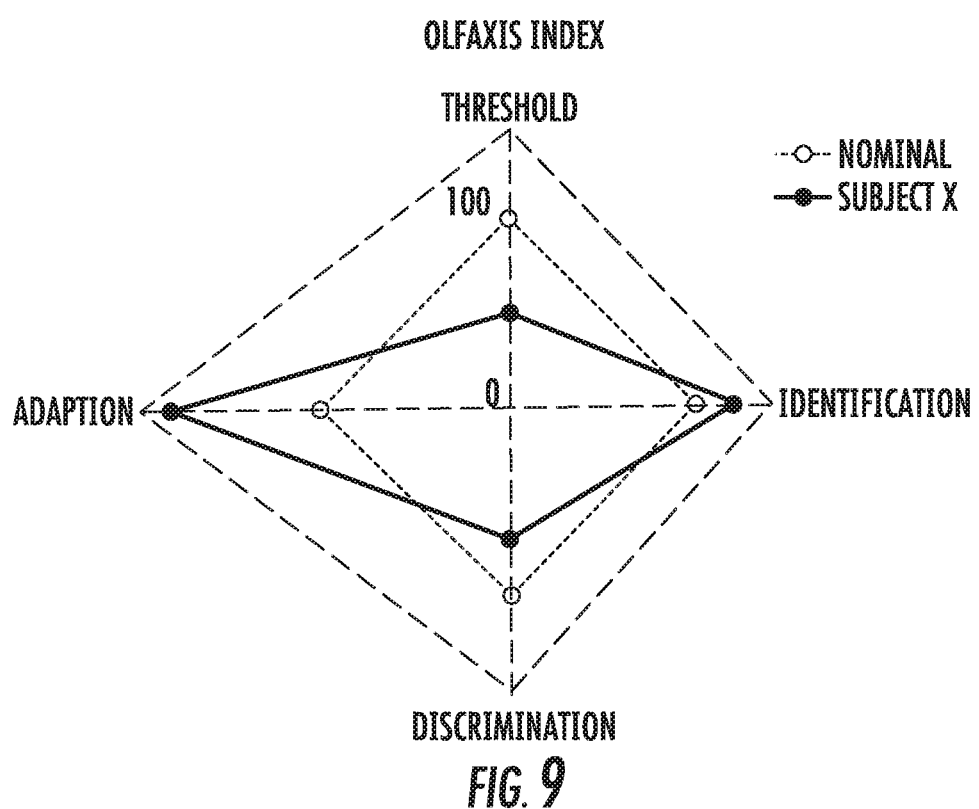
FIG. 9 is a graph of an Olfaxis Index that can be calculated based on the four different parameters shown in FIG. 8 for evaluating the subject based on a baseline measurement or a standard population norm according to embodiments of the present invention.

Referring to FIG. 9, discrete performance measures of each of the four olfactory functions can be obtained using the test systems and protocols discussed herein. FIG. 9 is an example image that shows an individual's performance on each of the four tests relative to a nominal value for a population or a population norm.

Some embodiments contemplate assessing threshold relative to OID, that is, for example, if threshold is the same, but OID varies over time, particularly above or below certain defined thresholds and/or amounts, then this may be predictive of eventual onset of AD or PD (suggesting more extensive testing or monitoring, for example).

The Olfaxis Index can be calculated using performance measures as a combination of multiple functional tests, each having an associated numerical value associated with a measurement of functional status.

Examples $$\text{Weighted: } a \cdot \text{Detection} + b \cdot \text{Discrimination} + c \cdot \text{Identification} + d \cdot \text{Adaption} \quad 1)$$

a. Detection, Discrimination, Identification, and Adaptation are the test subject's score on the specific functional test. These values may be raw or normalized for a population.

b. Scale factors a, b, c, and d may be any numerical value. Typically they will be positive numbers, but may also be 0 or negative. Scale factors a, b, c and d can have different numerical values.

$$\text{Power: Detection}^w + \text{Discrimination}^x + \text{Identification}^y + \text{Adaptation}^z \quad 2)$$

a. Detection, Discrimination, Identification, and Adaptation are the test subject's score on the specific functional test. These values may be raw or normalized for a population.

b. Exponents w, x, y, and z may be any numerical value. Typically, they will be positive numbers, but may also be 0 or negative. Exponents w, x, y and z can have different numerical values.

$$\text{Combined: } a \cdot \text{Detection}^w + b \cdot \text{Discrimination}^x + c \cdot \text{Identification}^y + d \cdot \text{Adaptation}^z \quad 3)$$

4) Any mathematical combination of the four individual test scores that provides meaningful and distinct statistically valid grouping between test subjects can be used for calculating the numerical Olfaxis Index. This Index may be provided with standardized score ranges, such as 0-1, 0-10, −10 to +10, or 0-100, for example, with lower or higher ranges associated with increased risk of neurological impairment, decline or disorder. See also, OI discussion described in PCT/U.S.2016/025519, filed Apr. 1, 2016, which is hereby incorporated by reference in its entirety.

Figure 10:
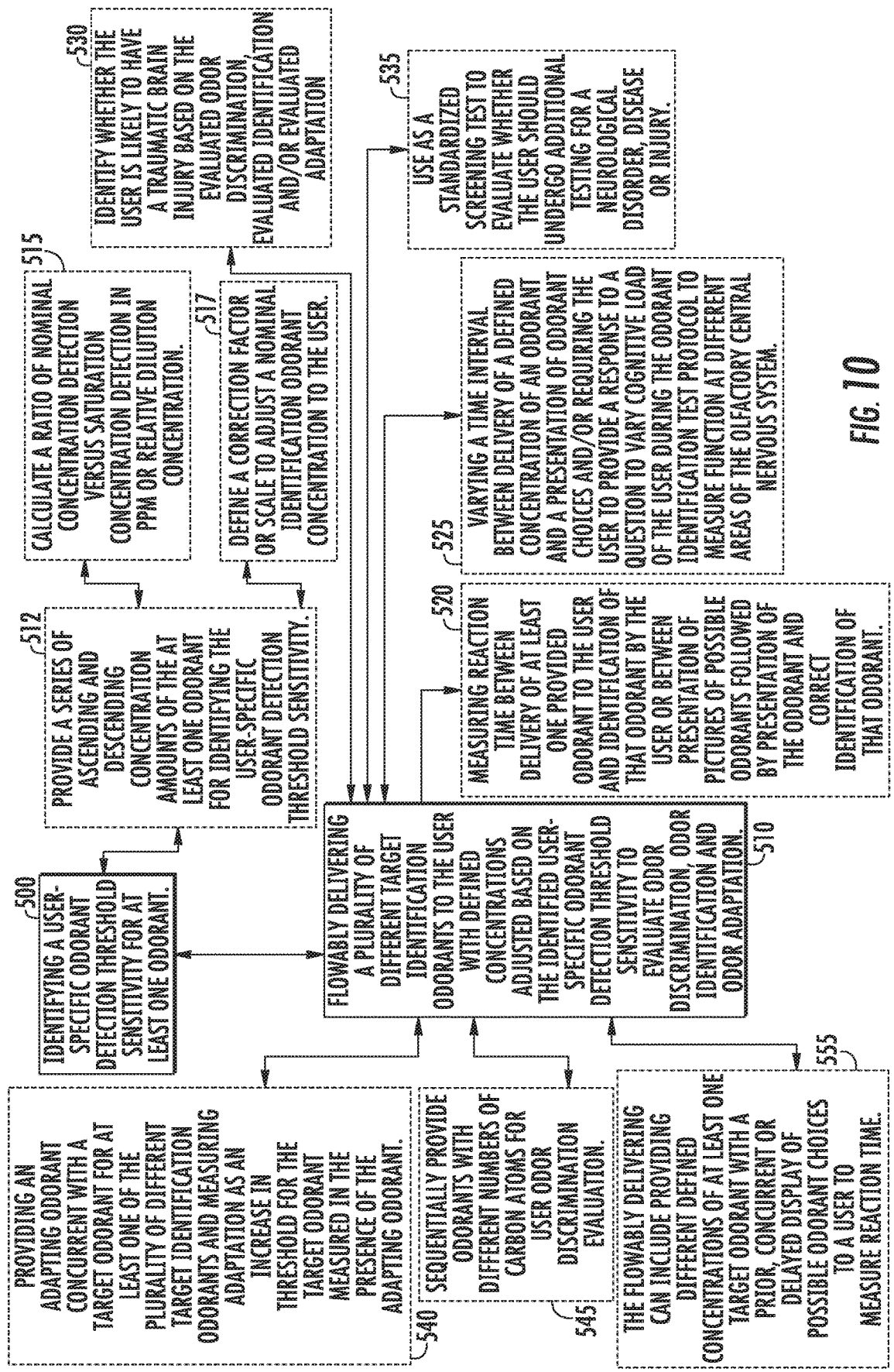
FIG. 10 is a flow chart of exemplary actions that can be used to evaluate olfactory function according to embodiments of the present invention.

FIG. 10 is an example flow chart of a test of olfactory function. A user-specific odorant detection threshold sensitivity for at least one odorant can be identified (block 500). A plurality of different target identification odorants can be flowably delivered to the user with concentrations adjusted based on the identified user-specific odorant detection threshold sensitivity to evaluate odor discrimination, odor identification and odor adaptation (block 510).

A series of ascending and/or descending concentration amounts of the at least one odorant for identifying the user-specific odorant detection threshold sensitivity can be provided (block 512).

A ratio of nominal concentration detection versus saturation concentration detection in ppm or relative dilution concentration can be calculated (block 515).

A correction factor or scale to adjust a nominal identification odorant concentration of, that user can be calculated (block 517).

Reaction time between delivery of at least one provided odorant to the user and identification of that odorant by the user or between presentation of pictures of possible odorants followed by presentation of the odorant and correct identification of that odorant can be measured (block 520).

A time interval can be varied between delivery of a defined concentration of an odorant and a presentation of odorant choices and/or requiring the user provide a response to a question to vary cognitive load of the user during the odorant identification test protocol to measure function at different areas of the olfactory central nervous system (block 525).

Identify whether the user is likely to have a traumatic brain injury based on one or more of the evaluated odor discrimination, evaluated identification and/or evaluated adaptation (block 530).

The test can be a standardized screening test to evaluate whether the user should undergo additional testing for a neurological disorder, disease or injury (block 535).

An adapting odorant concurrent with a target odorant can be provided and adaptation can be measured as an increase in threshold for the target odorant measured in the presence of the adapting odorant (block 540).

Odorants with different numbers of carbon atoms for user odor discrimination can be sequentially provided to the user (block 545).

Different defined concentrations of at least one target odorant with a prior, concurrent or delayed display of possible odorant choices can be provided to a user to measure reaction time (block 555).

Figure 11:
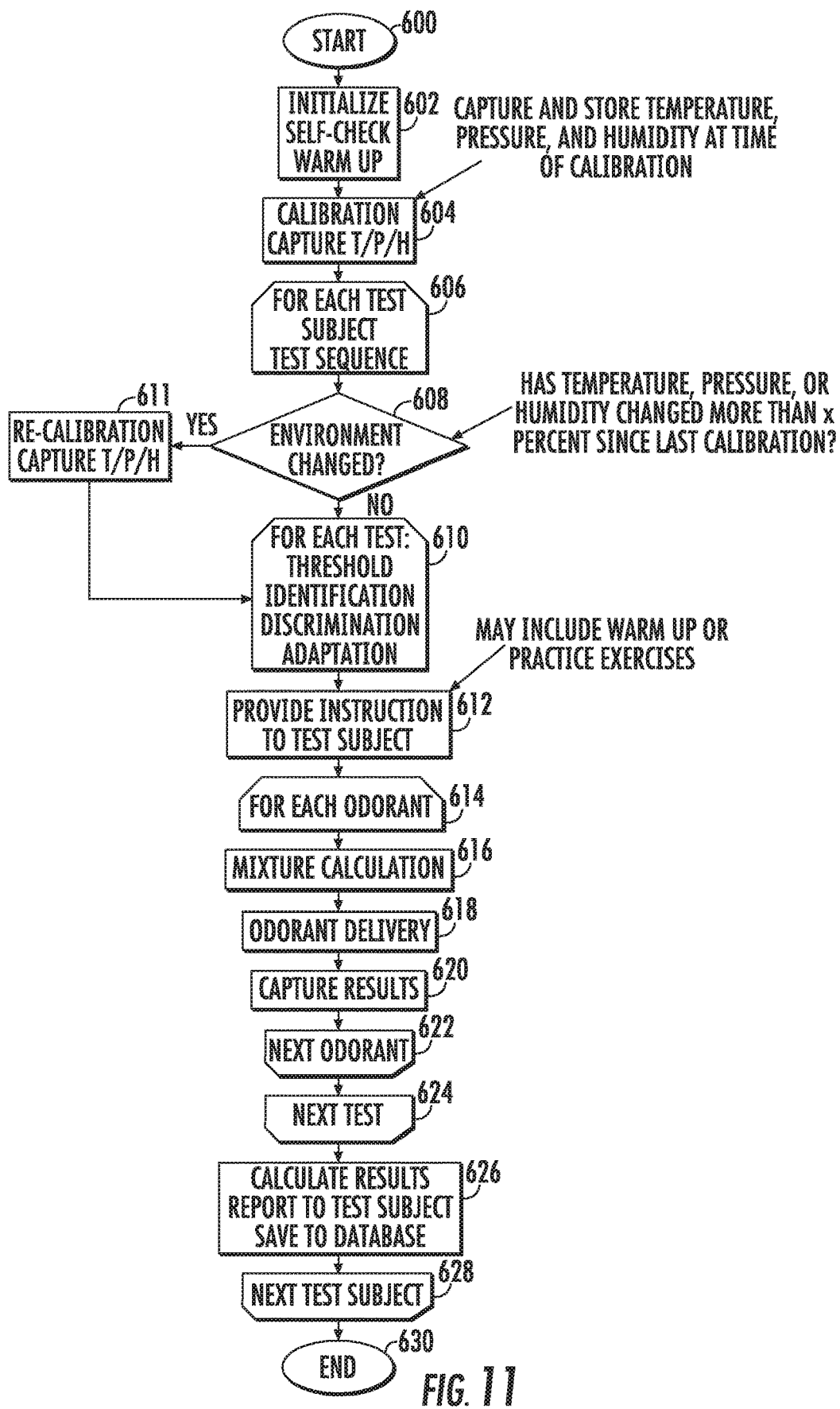
FIG. 11 is a flow chart of an exemplary test sequence that can be used to evaluate olfactory function according to embodiments of the present invention.
Figure 12:
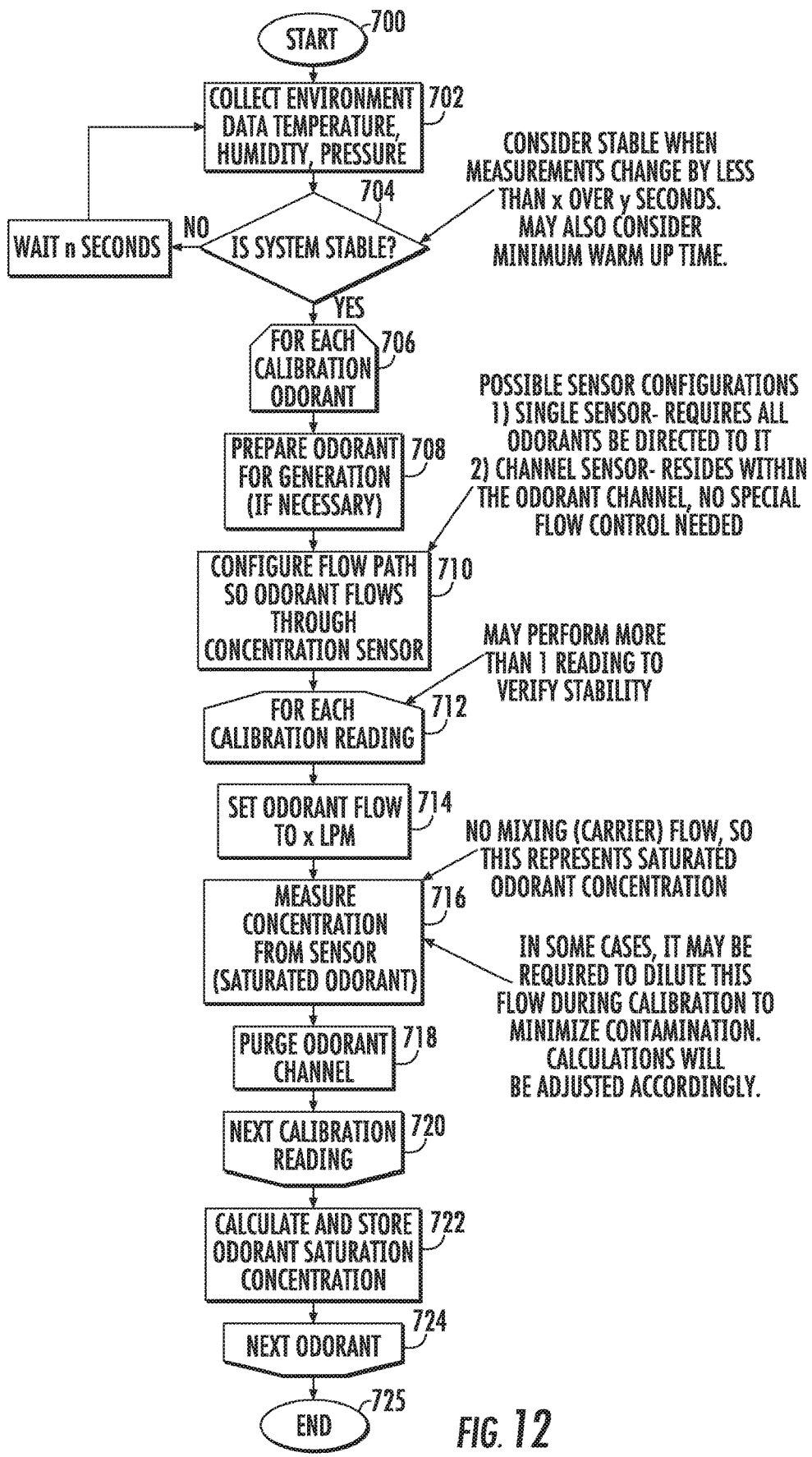
FIG. 12 is a flow chart of another exemplary calibration protocol according to embodiments of the present invention.
Figure 13:
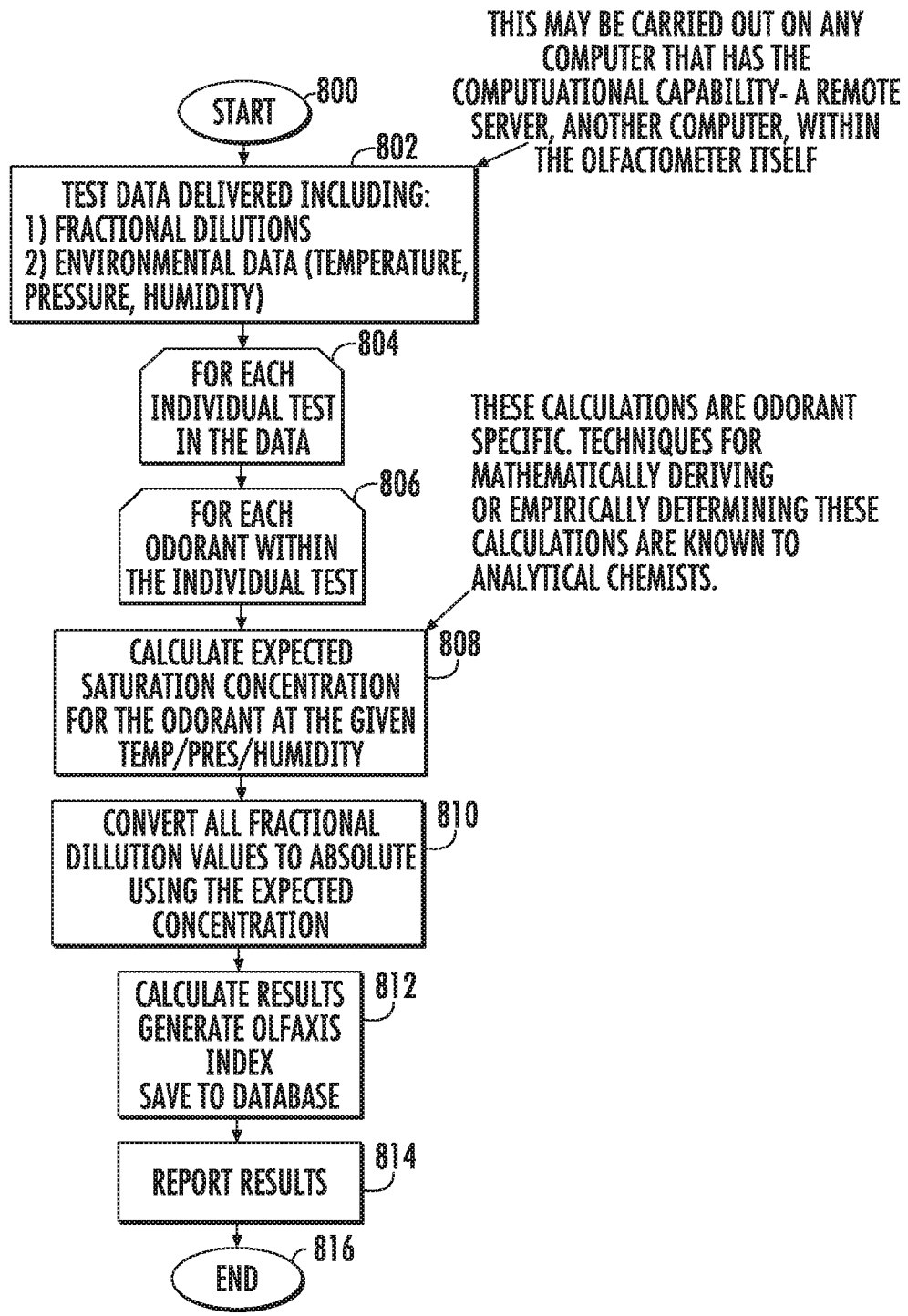
FIG. 13 is a flow chart of another exemplary calibration protocol according to embodiments of the present invention.
Figure 14:
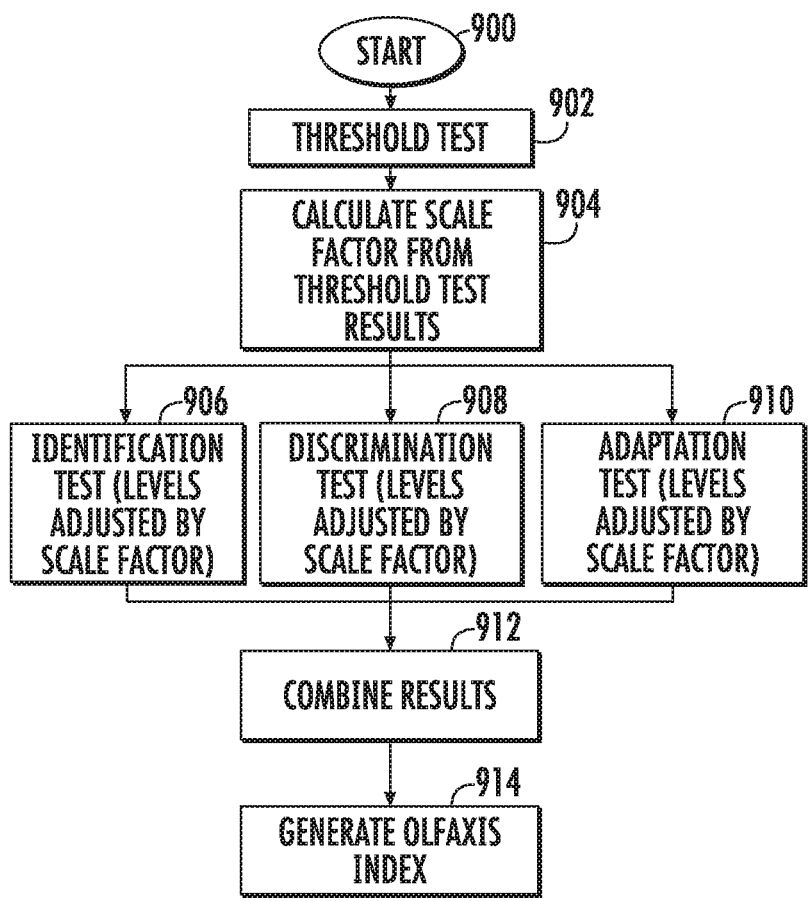
FIG. 14 is a flow chart of an exemplary olfactory test according to embodiments of the present invention.
Figure 15:
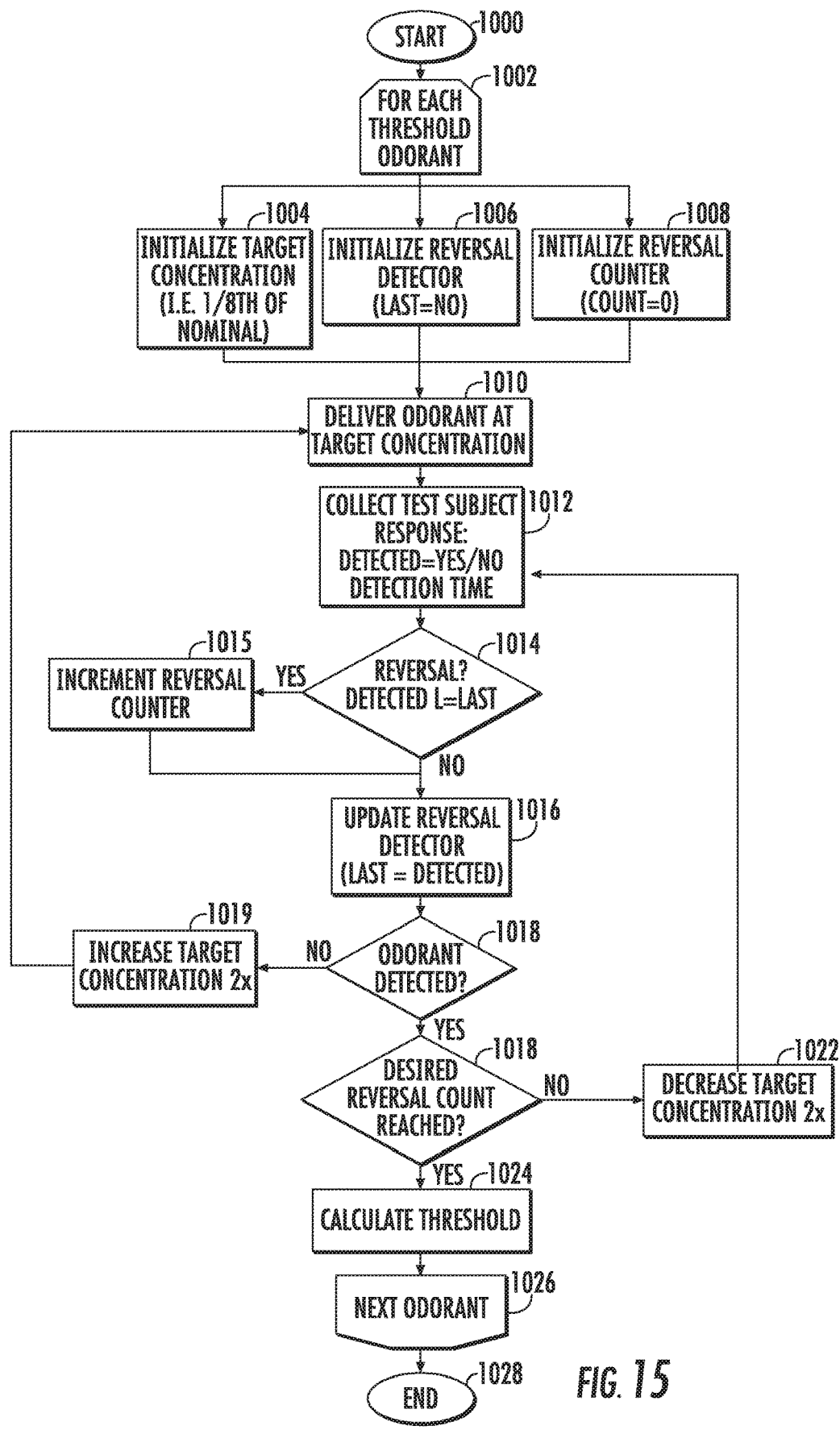
FIG. 15 is a flow chart of an exemplary threshold test according to embodiments of the present invention.
Figure 16:
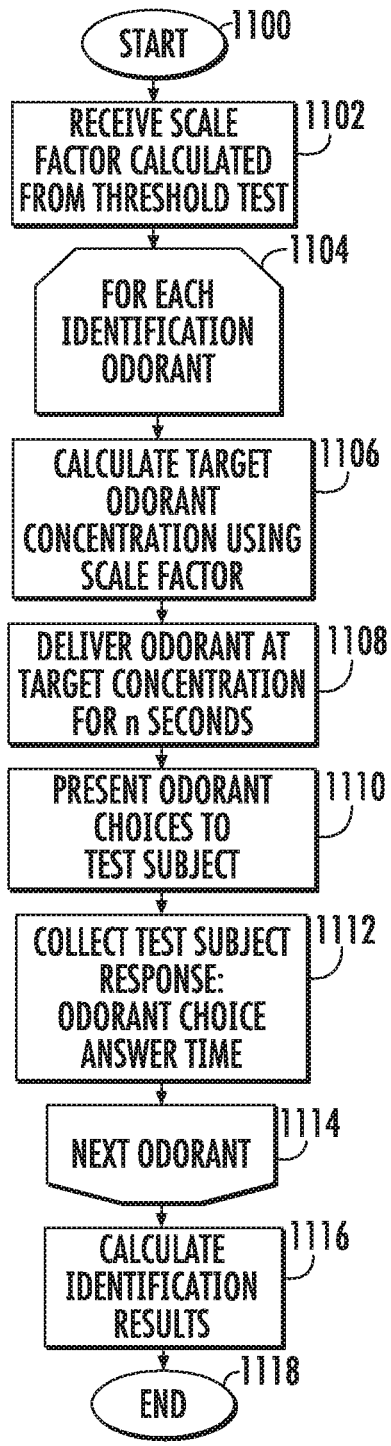
FIG. 16 is a flow chart of an exemplary identification test according to embodiments of the present invention.
Figure 17:
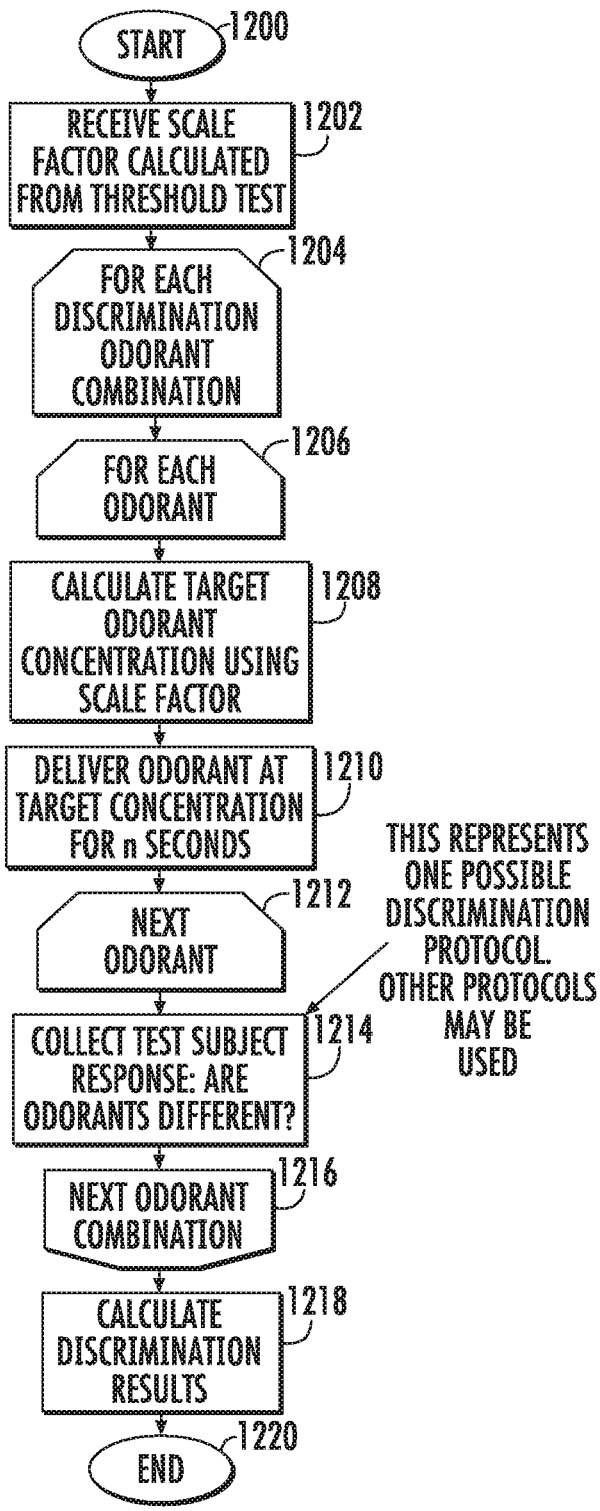
FIG. 17 is a flow chart of an exemplary discrimination test according to embodiments of the present invention.
Figure 18:
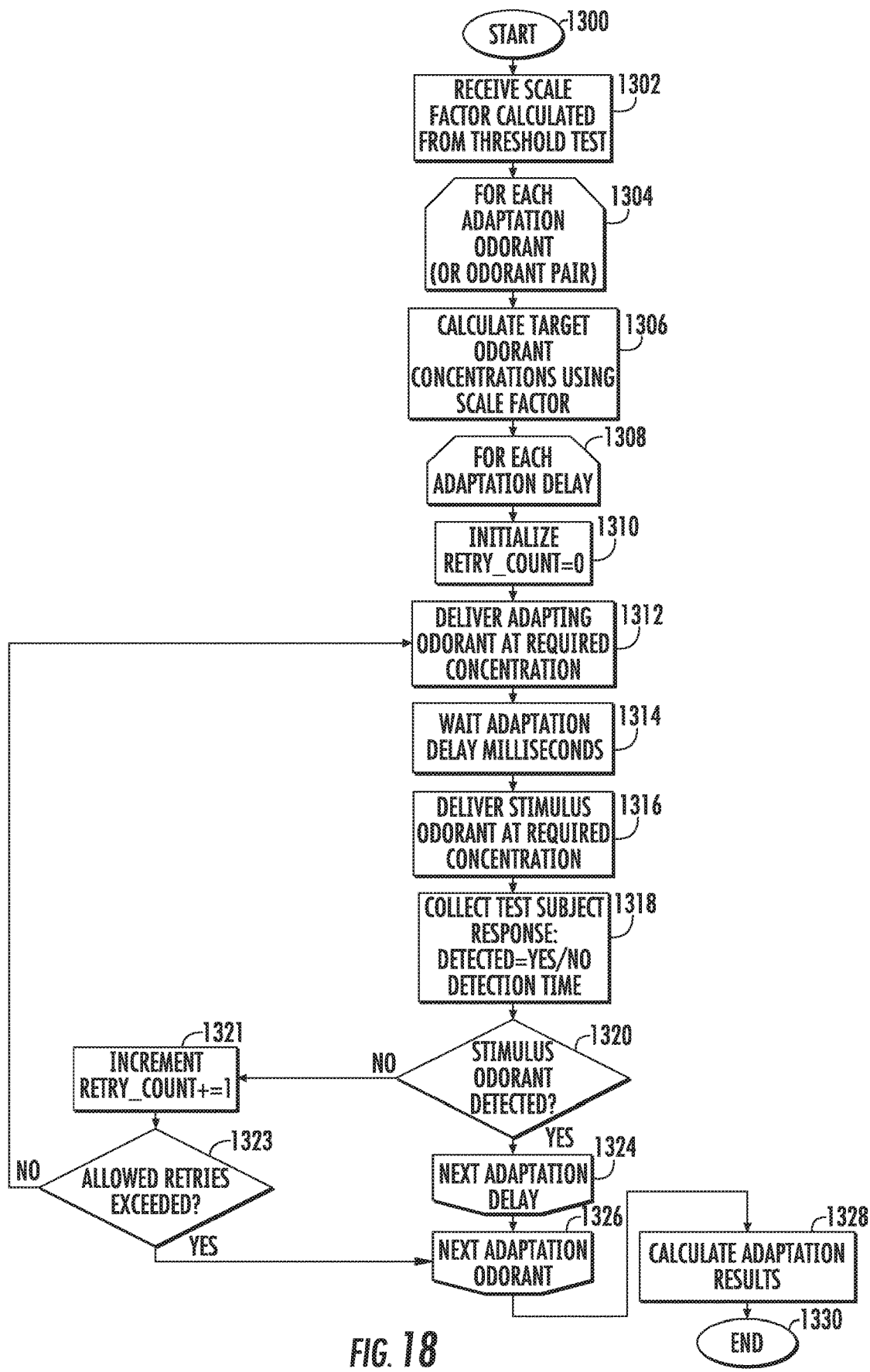
FIG. 18 is a flow chart of an exemplary adaptation test according to embodiments of the present invention.
Figure 19:
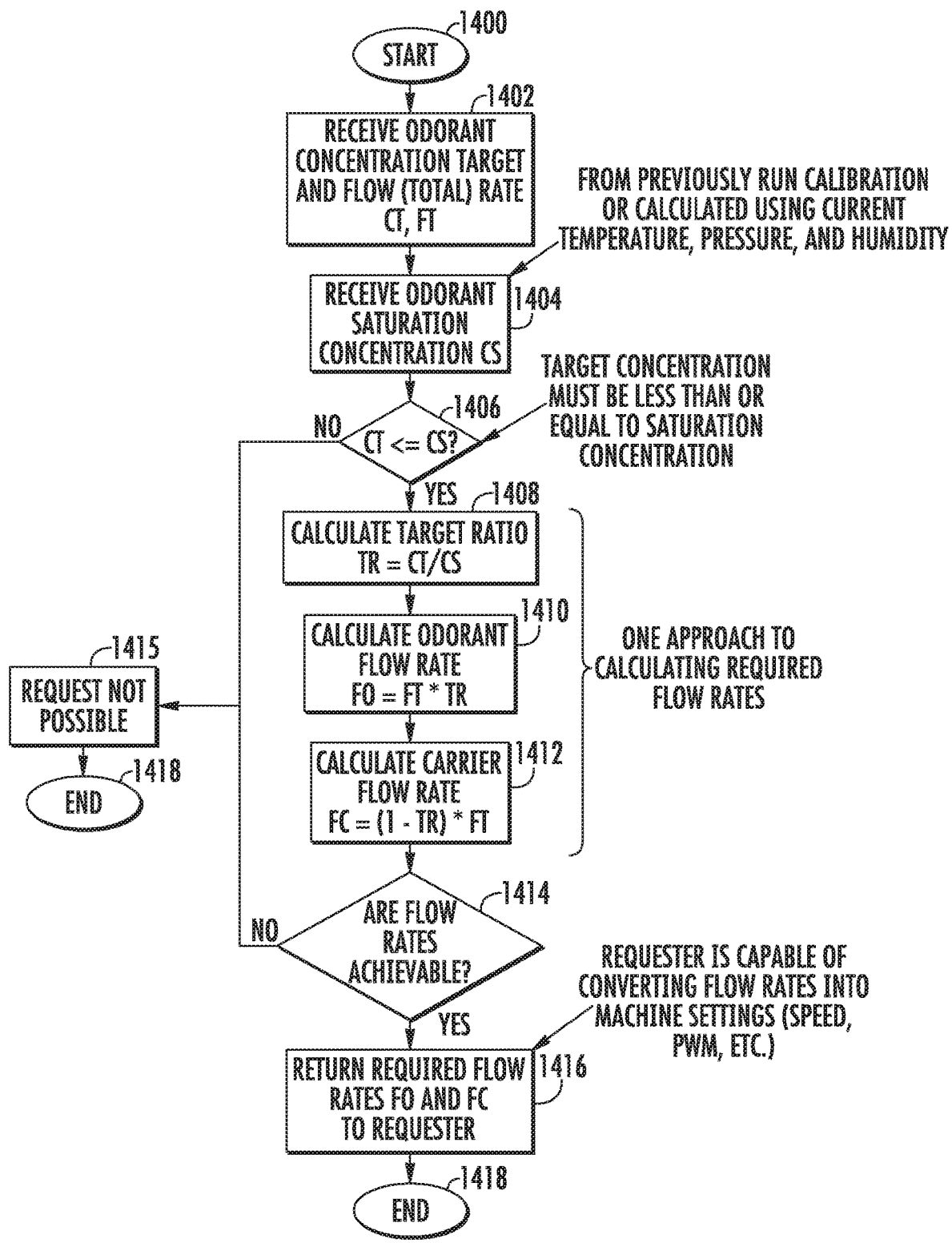
FIG. 19 is a flow chart of an exemplary mixture calculation that can be used for providing an olfactory test according to embodiments of the present invention.
Figure 20:
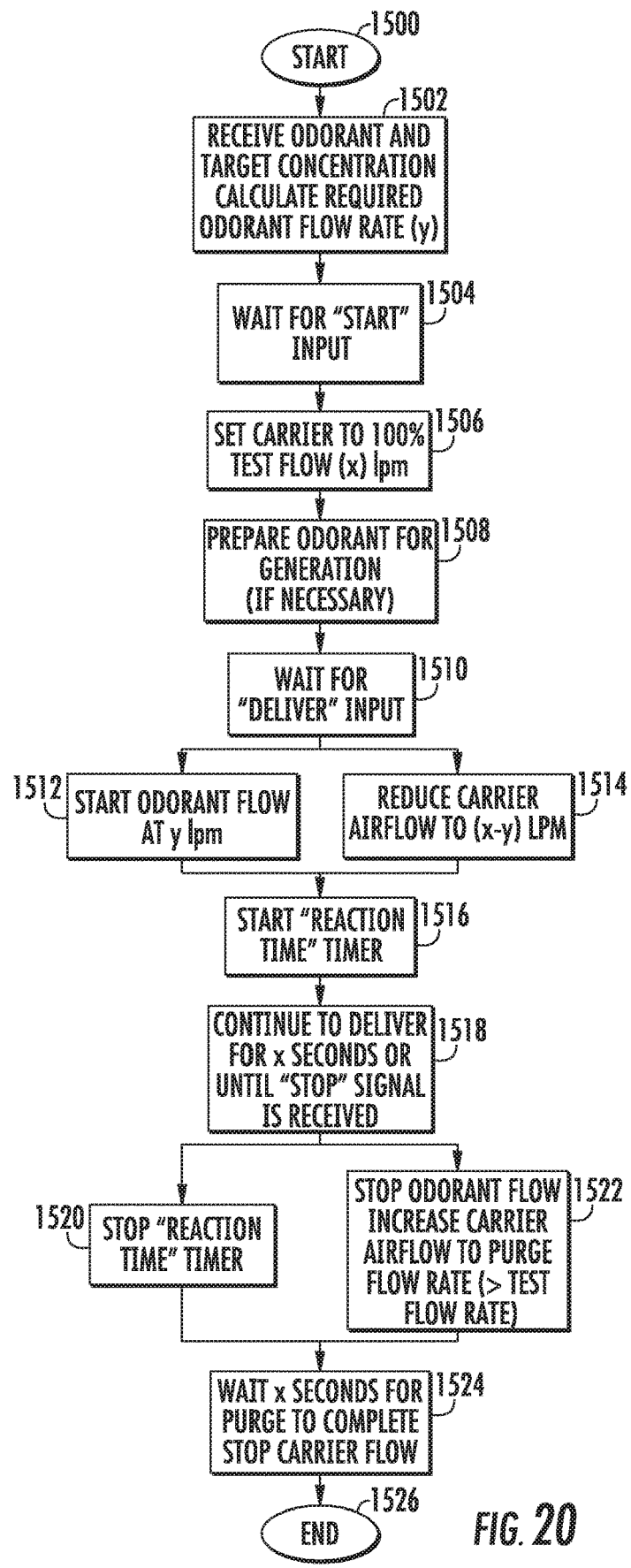
FIG. 20 is a flow chart of an exemplary odorant delivery sequence that can be used for an olfactory test according to embodiments of the present invention.

FIGS. 11-20 are flow charts of exemplary actions that can be carried out for testing olfactory function according to embodiments of the present invention. FIG. 11 illustrates actions associated with an exemplary overall test sequence of an exemplary olfactometer (blocks 600-630). FIG. 12 illustrates actions associated with a device calibration protocol for determining saturation of each odorant (blocks 700-725). FIG. 13 illustrates an alternate calibration protocol for converting test data from relative dilutions where calibration is not required to be on-board the olfactometer (blocks 800-816). FIG. 14 illustrates an exemplary test sequence of a target subject to generate an OI (blocks 900-914). FIG. 15 illustrates an exemplary threshold test to determine a detection threshold of one or more odorants by a user (blocks 1000-1028). FIG. 16 illustrates an exemplary identification test to evaluate the test subject's ability to identify an odorant from a set of choices (blocks 1100-1118). FIG. 17 illustrates an exemplary discrimination test for evaluating the test subject's ability to identify differences or similarities between odorants (blocks 1200-1220). FIG. 18 illustrates an exemplary adaptation test to evaluate the test subject's rate of adaptation for particular odorants (blocks 1300-1330). FIG. 19 illustrates an exemplary method for calculating odorant and carrier gas flow rates to deliver a calibrated odorant concentration (diluted from saturation) (blocks 1400-1418). FIG. 20 illustrates an exemplary method for delivering an odorant at a specific concentration to the test subject (blocks 1500-1526).

Figure 21:
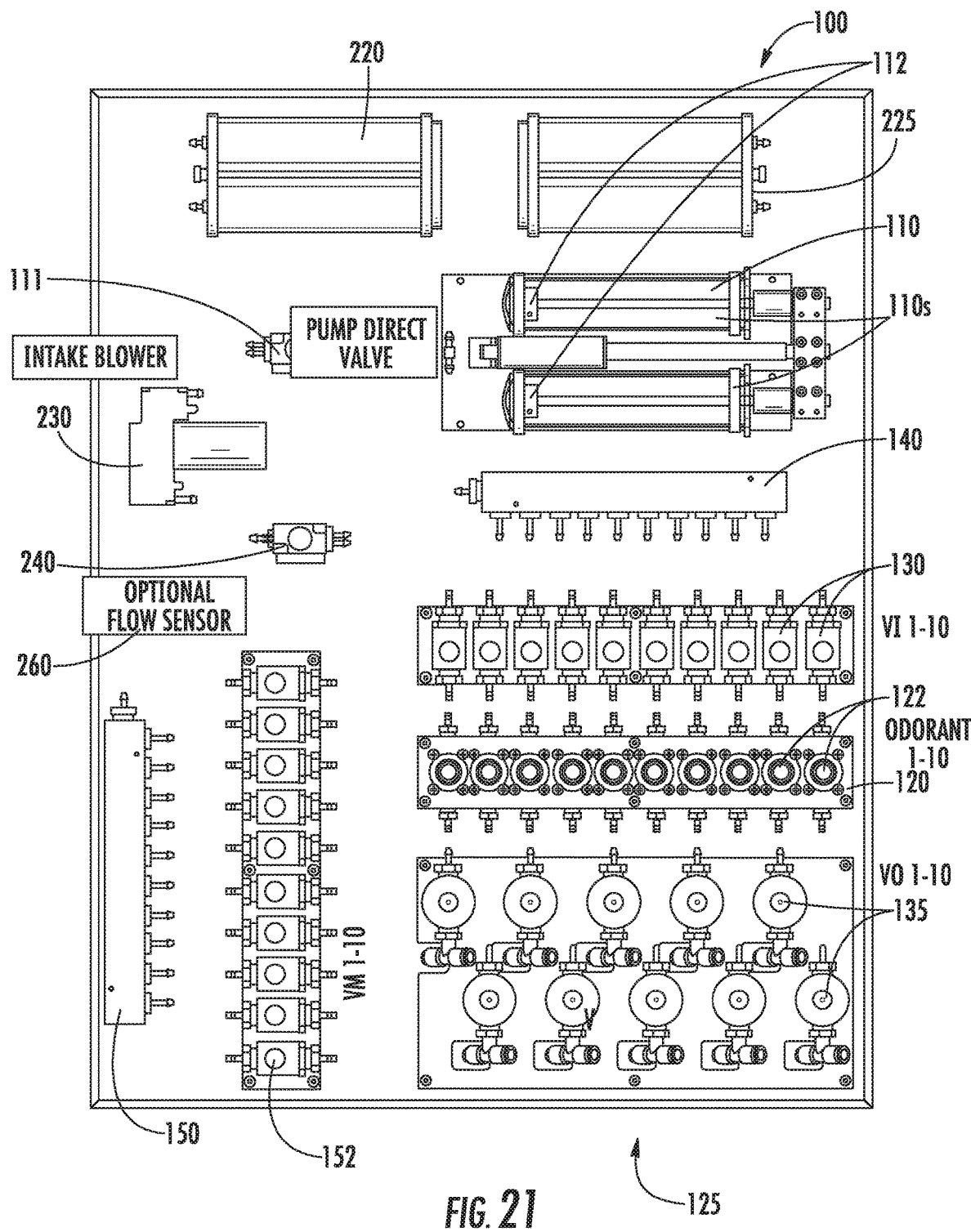
FIG. 21 is atop view of an odorant gas delivery system assembly according to embodiments of the present invention.

FIGS. 21 and 22 illustrate embodiments of an odorant gas delivery system 100 for the olfactory test systems 10 (FIG. 23A) for generating and delivering precise mixtures of an odorant and a carrier gas. However, the methods may be carried out using other suitable devices or test systems, such as those described in PCT/US2016/025519, filed Apr. 1, 2016, which is hereby incorporated by reference in its entirety.

The system 10 can include components that are cooperatively and operably connected to function together under the electronic commands of at least one system controller 25. Referring to FIGS. 21-23A, the system 10 can include an odorant gas delivery system 100 comprising a carrier gas supply 110, a fluid manifold 125 that may include an input distributor 140 and an output distributor 150, each in fluid communication with one or more odorant source devices 122. The fluid manifold 125 can include input valves 130 and output valves 135, one pair of an input and an output valve 130, 135, respectively, for each odorant source device 122. The output distributor 150 can be coupled via a fluid flow path 151 to a bank of manifold valves 152. As shown, one manifold valve 152*v* is coupled to each odorant exit flow path 126*e*.

The odorant chambers 122 can be provided as a unitary cartridge 120 with a rectangular perimeter that can be releasably coupled to the input and output valves for interchangeability of different cartridges 10 with different sets of odorants or with replacement sets of odorants as a consumable component of the test device.

The odorant source devices 122 hold defined stimuli odorants or adapting odorants in a solid, liquid or gas form. The fluid manifold 125 can include an output port or ports 155 that can be coupled to the conduit 12 that flow the carrier gas and odorant mixture to a nasal mask 15. The carrier gas can comprise air or any other suitable inert or noble gas(es), such as nitrogen.

The manifold 125 can have one or more flow paths 126 selected and active during a test sequence. The flow paths 126 shown by the arrows in FIG. 23A, include an intake side of the active flow path 126*i* residing upstream of a respective selected target odorant source device 122, which can have a sealed enclosed chamber, through an open valve 130 (VI) and a downstream side 126*e* through an open outlet valve 135 (VO). The exit flow paths 126*e* may be coupled to a transducer 170 such as an ultrasound transducer.

The system 10 can include an intake filter 220 and an output filter 225. The intake filter 200 can be in fluid communication with an intake blower, pump or fan 230 and an ambient air supply 110 as the carrier gas source. The output filter 225 can be coupled to the delivery mask 15 and may be in fluid communication with an output fan or blower 275. The source 110 can comprise ambient air or other inert gas or gases. The air and/or gas(es) can be filtered to remove impurities and may optionally be dehumidified or humidified to provide a clean gas at a predetermined humidity. This clean gas has two primary functions: 1) dilute the odorant to create known mixtures, and 2) purge the device to remove any residual odorant.

The filters 220, 225 can include desiccants, such as silica gel and the like, and sorbents, such as molecular sieve materials, carbon filters, polypropylene fiber, cellulose fiber, carbon dioxide filters (KOH, NaOH), etc.

The odorant gas delivery system 100 of the olfactory test system 10 can include a pump direction valve 111 and a carrier gas direction valve 240 and an optional flow sensor 260 in a flow path of the manifold 125. The pump direction valve 111 can be a three-way valve that can couple the carrier gas dispenser 110 such as at least one syringe 110*s* to a gas source in a first state for intake of carrier gas into the syringe 110*s*, then couple to the manifold 125 for directing the carrier gas to one or both of the input distributor 140 or the output distributor 150, depending on the state of the carrier valve 240. The flow of the carrier gas from the carrier direct valve 240 into the input distributor 140 and/or the output distributor 150, rather than into the syringe 110*s* or other gas dispenser 110 can be for purging/cleansing the flow paths.

The carrier gas dispenser 110 can comprise a fixed-volume flow controller as known in the art; basic components include a positive displacement pump, an actuator and a controller. By way of example and not limitation, the positive displacement pump may be selected from the group consisting of a piston pump, a plunger pump, and a diaphragm pump. The positive displacement pump can be connected to the motion-controlled actuator 113 (FIG. 23A) and the actuator can control the displacement distance and the displacement velocity of the piston, plunger or diaphragm with a high degree of precision. By controlling these two parameters, the actuator 113 can ensure that a predetermined volume of the gas is provided at a defined rate.

The carrier gas supply 110 can include at least one flow dispenser 111 such as at least one syringe 110*s* that can be operated by the actuator 113 to force a carrier gas to flow into a selected flow path or paths 126 of the fluid manifold 125 that is in fluid communication with the odorant chamber(s) 122 for delivering a defined volume of a carrier gas or an odorant at a defined flow rate. An active one or more selected flow path 126 can be defined by controllably opening an input valve 130 and an output valve 135 corresponding to (on opposing sides of) a desired odorant chamber 122 and flowing the carrier gas through that chamber 122 out the exit flow path 126e and to the conduit 12 and into the nasal mask 15.

An example flow dispenser 111 for the carrier gas supply 110 can include one or more of a piston pump, an actuator, a position sensor, an open loop actuator such as a stepper motor, control valves, controller, and a power source. The control valves can be activated by pressure, mechanical force, or electro-mechanical force. A position sensor may be used to indicate the physical position of the actuator and may be an encoder, potentiometer, LVDT, or any sensor capable of measuring linear position. The position sensor is read by the controller to determine position, and may be read during motion at known time intervals to determine velocity, acceleration, etc. Other components that can be used for alternative embodiments include one or more humidity sensors, temperature sensors, pressure sensors, or a variety of other sensors used to identify the state of the device. The actuator is any type of actuator that provides high accuracy, high precision displacement distance and displacement velocity. By way of example and not limitation, types of actuators suitable for use with the present invention apparatus include hydraulic, pneumatic, electric, thermal, or magnetic (shape memory alloys), and mechanical.

The flow-controllers contained within the device are sized so they can produce the required flow rate for the required time at a variety of concentrations. Flow rate and duration are chosen such that test subjects are presented with a sufficient volume of the mixture for a sufficient time to allow for identification. Example values are a rate of 5 liters per minute for duration of two seconds. The flow controllers may include additional capacity for other functions such as pre and post mixture flows and system purging.

In certain particular embodiments, as shown in FIGS. 21 and 22, the pressurized carrier gas supply 110 can comprise a plurality (shown as two parallel) of syringes 110s, optionally with side by side adjacent chambers 110c and plungers 112 concentrically therewithin ("carrier cylinders"), with coupled outputs which generates specific flow by first using plungers 112 to fill the carrier cylinders 110c with clean gas from a carrier gas source 120. An actuator 113 such as a linear actuator can control the motion of the plungers 112.

In some embodiments, a syringe is located upstream of one or more odorant source devices ("odorant generators") 122. The syringe 111s can be fluidly connected to a 3-way valve 111 which connects it to either 1) a clean air source or 2) the manifold 125 which includes an individual valve 130 or valve pair 130, 135, for each odorant generator. The upstream position of the syringe 110s in the fluid manifold 125 allows it to only contain clean air so it can be used to deliver a precise flow through any of the odorant generators without risk of cross contamination. In operation, the 3-way valve 111 first connects the syringe 110s to the clean air source. The syringe retracts and fills with clean air. The 3-way valve 111 then connects the syringe 110s to the manifold 125. When it is time to dispense, the valve(s) 130, 135 for the desired odorant opens to create a flow path 126 from the syringe 110s through the odorant generator 122. The syringe 110s dispenses at a specific speed which yields a specific flow rate of air through the odorant generator, where it becomes saturated with odorant vapor.

Mixing of multiple odorants can also be accomplished by test systems 10 according to embodiments of the present invention. For example, the test systems 10 can comprise at least two syringes 110s (or other flow controllers) in fluid communication with the manifold 125. Each syringe 110s can be fluidly connected to a different one of the odorant generators 122, and mixing is accomplished by dispensing each syringe 110s at the desired rate. The also creates the ability to include a delay between delivering each odorant by controlling the start of motion of each syringe 110s.

FIGS. 24A-24E illustrate embodiments of an odorant gas delivery system 100 each of which may be provided as a cartridge 120 (FIG. 22).

Figure 24A:
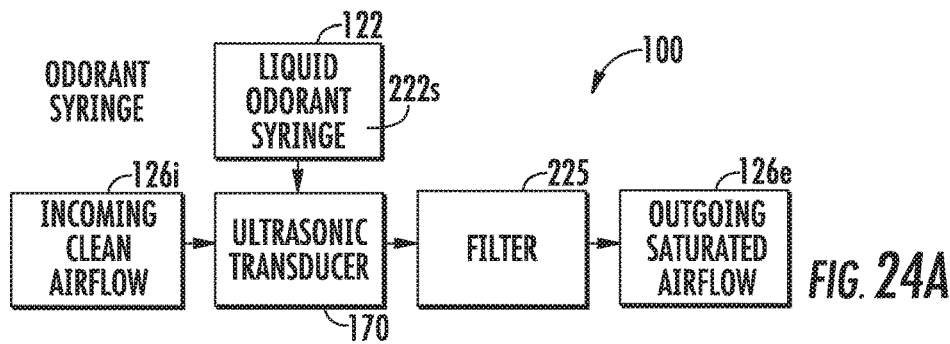
FIGS. 24A-24E are schematic illustrations of odorant generation systems according to embodiments of the present invention.

Referring to FIG. 24A, the odorant gas delivery system 100 can include odorant source devices 122 that comprise odorant syringes 222s. For this embodiment, odorant can be stored in a syringe 222s that dispenses directly on to an ultrasonic transducer 170, where it can be rapidly (immediately) vaporized. Airflow from inlet path 126i passes over the transducer 170 where it picks up micro-droplets which can quickly evaporate to saturate the airflow as outgoing saturated airflow in the outlet flow path 126e.

Figure 24B:
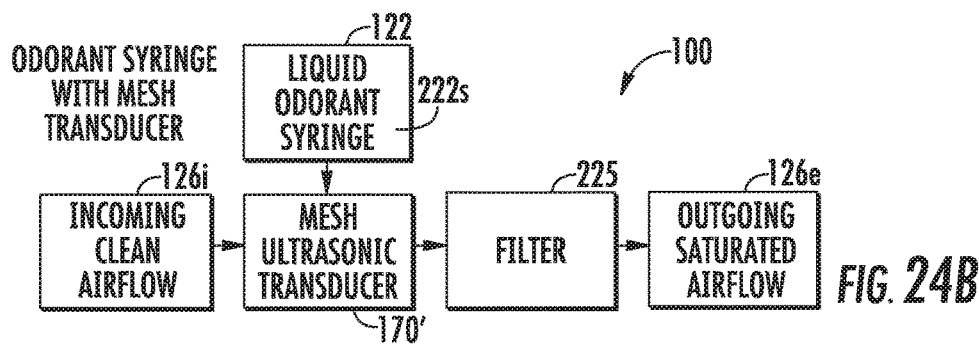

In other embodiments, as shown in FIG. 24B, the odorant source devices 122 can be in fluid communication with mesh ultrasonic transducers 170'. In this embodiment, a single odorant dose can be delivered to a mesh transducer 170' by a syringe 222s where it disperses via capillary action. The mesh transducer 170' can be energized and airflow from the inlet airflow path 126i passes over it where it picks up the micro-droplets which quickly evaporate to saturate the airflow as outgoing airflow in the exit flow path 126e. A mesh transducer 170' may be efficient at vaporizing small amounts of odorant.

Figure 24C:
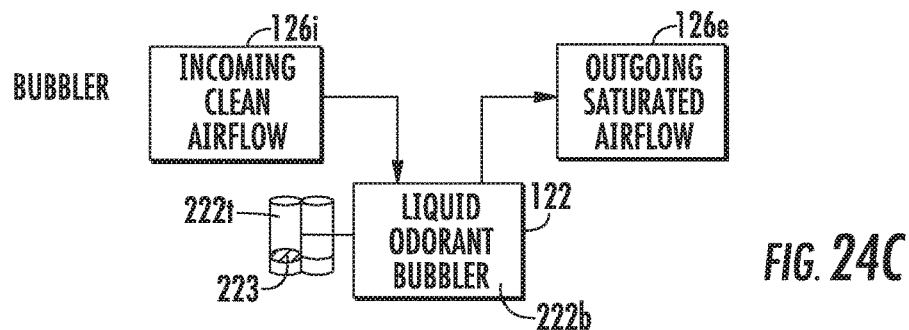

Referring to FIG. 24C, in some embodiments, the odorant gas delivery systems 10 can comprise odorant source devices 122 that comprise compact bubblers 222b. These compact bubblers 222b can be configured as one or more (small diameter) tubes 222t, typically oriented upright or vertically, that contain the odorant 122. Airflow enters the bottom of the tube through a screen 223 which creates many small bubbles. These bubbles flow up through the odorant and saturate with vapor. The saturated airflow exits at the top of the tube. This configuration reduces risk of un-evaporated droplets leaving the cartridge 120.

Figure 24D:
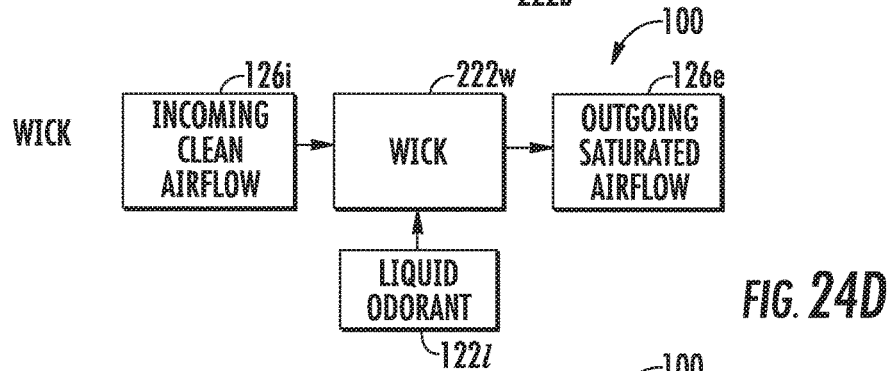

Referring to FIG. 24D, in some embodiments, the odorant source devices 122 can comprise a wick 222w which can be a felt-like wick material in contact with liquid odorant 122l. The wick 222w may be flat, cylindrical (solid or semi-solid), hollow cylindrical, pleated, etc. Airflow travels through/near the wick 222w to pick up odorant vapor and become saturated. The wick 222w can be configured to move in and out of the odorant liquid (in for storage, out for dispense). This configuration may provide a relatively large surface area for odorant reducing any risk of un-evaporated droplets.

Figure 24E:
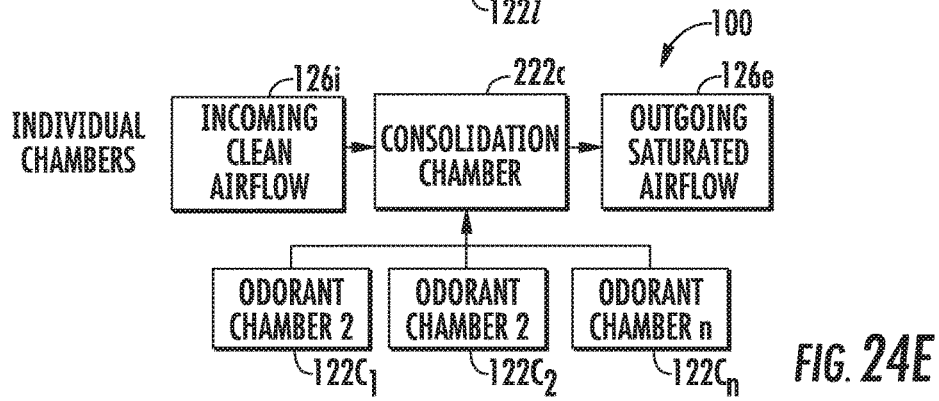

Referring to FIG. 24E, in some embodiments, the odorant source devices 122 can comprise odorant chambers $122c_1$, $122c_2$, $122cn$—where target odorant can be stored in multiple independent chambers, typically of the same known volume, and where n=any suitable number of chambers, typically from 3-100, more typically from 3-12. Each individual volume can be capable of mixing with x ml of clean carrier gas such as air in a consolidation chamber 222c, such that y concentration is created. Odorant gas from these chambers $122c_1$, $122c_2$, $122cn$ may be released (one or more). For example—the individual chambers contain 1 ml of 1000 ppm odorant. Two chambers can be released and mixed in a consolidation chamber 222c with 98 ml of clean air, creating 100 ml of 20 ppm odorant.

The gas delivery systems 100 can be configured so that un-evaporated droplets do not leave the exit flow path 126e, cartridge 120 or respective source device 122. For example, the system 10 can include one or more of:

a. Filter—catch droplets in the filter(s)
b. Bubbling—bubbling techniques do not create droplets in the first place.
c. Trap—use droplets techniques, but direct the airflow through an odorless liquid trap (mineral oil) that will capture any un-evaporated droplets. The trap can be integrated into the cartridge 120.

It is noted that the carrier fluid does not have to be generated by fixed-volume flow controller. It may be generated by a pump, fan, etc. Any flow-producing mechanism that can produce precise and repeatable flows can be used. A flow sensor can be incorporated for feedback and closed-loop flow control.

Concentration may be measured by an on-board one or more concentration sensor S. Odorant flows may be directed to this sensor S for concentration verification or calibrations. As shown in FIG. 23A, a sensor S may be included for each individual odorant source device 122 or exit flow path 126e. FIG. 23B illustrates a headspace 170h with a saturated concentration Cs of odorant in fluid communication with the flow path 126 and coupled to an aerosolization device such as the ultrasonic transducer 170.

Instead of directly measuring saturation concentration, prior to testing, embodiments of the invention can determine saturation levels as a function of temperature, humidity and pressure. These environmental conditions can be measured within the device 10 and these measurements can be used to calculate expected saturation concentration. The mixing ratios can be adjusted to hit target concentrations (typically precisely and reliably).

The odorant assembly generates a volume of chemical odorant at a requested concentration and delivers that volume at a requested flow rate. Each odorant assembly includes an odorant source, such as a disposable cartridge or glass ampule, a fixed-volume flow controller, and valves to facilitate odorant generation and dispensing. In an alternative embodiment, the odorant assembly includes a temperature sensor to determine the temperature of the odorant. The odorant dispenser is connected to the carrier gas conduit in order to receive the carrier gas for the purpose of diluting the odorant.

Preferably, the odorant source devices 122, cartridges 120 are single use, disposable, and/or injection molded.

Referring to FIG. 23A, in some embodiments, with valves 130, 135 closed, there is no flow path through to exit flow path 126e. The exit flow path 126e is preferably as short as possible although shown as relatively long for illustration purposes.

The odorant source devices 122 contain the odorant, typically comprising a volatile chemical(s) of interest, most often in a liquid form, although a compressed gas form is provided for herein; and can be pure or diluted in another substance, such as water, diethyl phthalate, mineral oil, another carrier gas in the case of a compressed gas form, etc. The odorant source can be configured in an amount intended for single use or for multiple uses. In preparation for mixture creation, some of the chemical source may be converted from liquid to vapor. This conversion may be natural (diffusion) or accelerated through artificial means, such as ultrasonic vibration, heat, and the like. The conversion is designed to create a known volume of a known concentration of the odorant vapor.

The odorant generated by this process represents the highest concentration of the chemical that may be achieved, limited by the physical properties of the chemical and the environmental conditions.

Mixing

The odorant vapor from the odorant source device(s) 122 can be mixed with clean gas to produce mixtures of lower concentration. Precise mixtures are created by dispensing the odorant vapor and clean carrier gas at specific rates and mixing their outputs.

In some embodiments, mixtures can be created by the following steps:

1) Generating an odorant vapor by flowing carrier gas through an odorant source device 122
2) Filling a clean gas dispenser
3) Calculating a flow-controller speed to generate the desired odorant/carrier gas ratio. For example:
a. Target is a 25% mixture of chemical A.
b. Calculate the vapor pressure of chemical A at the current environmental conditions, and determine that it will yield a 50% mixture in the odorant dispenser.
c. Given the odorant % and the target %, the flow ratio may be calculated by
   i. $r_{flow} = (p_{odorant}/p_{target}) - 1$
   ii. $r_{flow} = (50\%/25\%) - 1$
   iii. $r_{flow} = 1$
d. This means the clean gas flow rate should equal the odorant flow rate.
e. Given the total flow rate, calculate the flow rates for the carrier gas and the odorant vapor.

In some embodiments, the olfactometer 10 can comprise at least one odorant concentration sensor 299, which can optionally comprise a photoionization detector (PID, as shown in FIG. 23A. The odorant concentration sensor 299 can reside in an exit flow path 126e, typically prior to the delivery device 15 and downstream of the manifold 150, where used. Each odorant generation module associated with a respective odorant delivery source 122 can have an odorant concentration sensor 299. In practice, the at least one odorant concentration sensor 299 concentration sensor (PID is one form) may not be used on every odorant generation/dilution but can be used in an initial calibration step. Saturation concentration should remain constant with constant temperature, pressure and humidity. The olfactometer system 10 can monitor and/or record these values during calibration and can continue to monitor them during testing, optionally forcing a new calibration if concentration values vary outside a predicted range and/or if local environmental parameters, for example, change.

Referring again to FIG. 23, in some embodiments, an intake blower 230 pulls carrier gas, preferably air, in through an input filter 220. A flow sensor 260 detects carrier gas flow. A carrier direct valve 240 sends the carrier gas to either an input distribution manifold 140 or an output distribution manifold 150.

An odorant positive displacement pump 325 intakes the carrier gas through the input filter 220. An odorant positive displacement pump direct valve 111 allows carrier gas intake from the carrier gas filter 220 into the positive displacement pump 110s when the positive displacement pump direct valve 111 is in intake position. Upon switching to expel position, the positive displacement pump direct valve 111 is set to route carrier gas to the input distribution manifold 140. The blower 230 and odorant positive displacement pump 110s are both connected to the input distribution manifold 140. Odorant is contained in at least one odorant container 122 and prevented from diffusing by inlet valves VI 130 and outlet valves VO 135.

From the input distribution manifold 140, the carrier gas goes through one or more of the at least one odorant containers 122, picking up odorant, and becoming an odorant-carrier gas mixture. The routing of active flow paths through the odorant containers is determined by the settings of the inlet valves VI (337) and outlet valves VO (340).

Carrier gas from the output distribution manifold 150 can be joined with odorant-carrier gas mixture exiting the odorant containers 122. The carrier gas from the output manifold 150 can dilute the odorant-carrier gas mixture to the desired concentration. Flow of carrier gas into an exit flow path 126e is controlled by its respective manifold valve VM 152.

The mixed air is routed to the mask 15, then vacuumed out through an output filter 225 by an output blower 275.

A controller 25 controls all the components. The controller is local or remote, wired or wireless.

The carrier flow can be provided by a blower 230 instead of or with a piston. The carrier flow can be measured by a flow sensor 260, and this feedback is used to control the actuator that dispenses precise flow control. The odorant positive displacement pump (i.e., syringe) 110s never contains odorant vapor. It pushes a precise clean airflow through one of many odorant sources such that the airflow is saturated with vapor when it exits the odorant chamber. It is then mixed with the carrier flow to produce the desired mixed flow.

Multiple Odorant Mixtures, Delayed Onset and Adaption

The system is also configured to provide multiple odorants simultaneously or sequentially. When mixing multiple odorants, the system controller provides for adjusting the carrier gas and individual odorant flows so that the maximum system flow capacity is not exceeded and the multiple odorants are at the desired concentrations.

The system also provides for sequential or delayed addition of odorants to the carrier gas. By way of example and not limitation, a second odor is added one (1) second after the first odor was introduced into the carrier gas.

In some cases, it is desirable to mask certain changes in the device operation from the test subject, in order to prevent the subject from making guesses as to when certain events occur, such as the start of an odorant flow or the addition of a secondary odorant. Changes may be inadvertently communicated to the test subject via changes in air flow, changes in sound, etc. Techniques to mask such changes may include concealment or misdirection. Concealment examples include 1) precise control over component flows (carrier and odorants) so the total flow rate does not change, for example as a first component flow increases a second component flow decreases at the same rate to maintain a consistent total; and 2) using silent actuators or sound insulation to prevent the test subject from hearing the internal operations of the device. Misdirection examples include 1) deliberate inconsistency in the odorant flow (pulsing) so changes are not distinguishable or 2) including a placebo flow which does not contain any particular odorant, while maintaining the same operation as the real odorants.

The above-mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the present invention. Such modifications and improvements include replacing "odor" or "odorant" with "vapor" and/or "gas." Additionally, while the term "solenoid" is used throughout the specification, other embodiments of the present invention include other means for controlling valves such as a thread and nut system, a linear actuator, or another magnetic coil system.

The test system may communicate with or be embodied as a standalone server or may be contained as part of other computing infrastructures. The test system may be embodied as one or more enterprise, application, personal, pervasive and/or embedded computer systems that may be standalone or interconnected by a public and/or private, real and/or virtual, wired and/or wireless network including the Internet, and may include various types of tangible, non-transitory computer-readable media. Different test systems can communicate with the network via wired or wireless connections, and may include various types of tangible, non-transitory computer-readable media. The test systems can be provided using cloud computing which includes the provision of computational resources on demand via a computer network. The resources can be embodied as various infrastructure services (e.g., compute, storage, etc.) as well as applications, databases, file services, email, etc.

Figure 25:
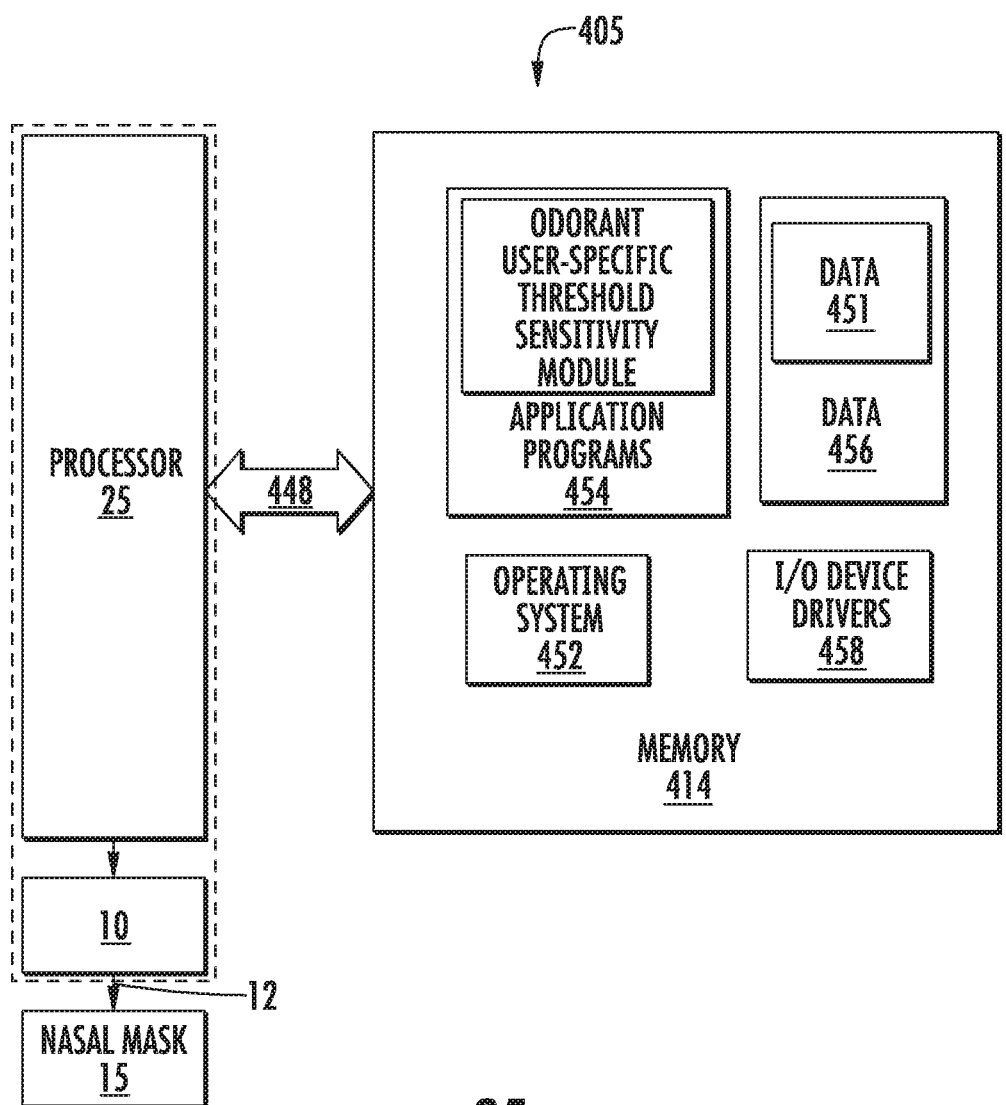
FIG. 25 is a box diagram of a data processing system for an olfactory test system according to embodiments of the present invention.

FIG. 25 is a block diagram of exemplary embodiments of data processing systems 405 in accordance with embodiments of the present invention. The processor 410 communicates with the memory 414 via an address/data bus 448. The processor 410 can be any commercially available or custom microprocessor. The memory 414 is representative of the overall hierarchy of memory devices containing the software and data used to implement the functionality of the data processing system 405. The memory 414 can be non-transitory, and can include, but is not limited to, the following types of devices: cache, ROM, PROM, EPROM, EEPROM, flash memory, SRAM, and DRAM.

As shown in FIG. 25, the memory 414 may include several categories of software and data used in the data processing system 405: the operating system 452; the application programs 454; the input/output (I/O) device drivers 458; an automated User-Specific Threshold Sensitivity Calculation Module 450 and the data 456.

The data 456 may include a defined staircase sequence of different concentrations for delivering different concentrations of odorant for estimating the user-sensitivity threshold. The data can comprise a look-up chart of different odorant parameters, such as fractional dilution values and expected saturation concentration, potentially correlated to or based on humidity, pressure and/or temperature used for calibration of concentration of odorant mixtures.

As will be appreciated by those of skill in the art, the operating system 452 may be any operating system suitable for use with a data processing system, such as OS/2, AIX, DOS, OS/390 or System390 from International Business Machines Corporation, Armonk, NY, Windows CE, Windows NT, Windows95, Windows98 or Windows2000 from Microsoft Corporation, Redmond, WA, Unix or Linux or FreeBSD, Palm OS from Palm, Inc., Mac OS from Apple Computer, LabView, or proprietary operating systems. The I/O device drivers 458 typically include software routines accessed through the operating system 452 by the application programs 454 to communicate with devices such as I/O data port(s), data storage 456 and certain memory 414 components. The application programs 454 are illustrative of the programs that implement the various features of the data processing system 405 and preferably include at least one application which supports operations according to embodiments of the present invention. Finally, the data 456 represents the static and dynamic data used by the application programs 454, the operating system 452, the I/O device drivers 458, and other software programs that may reside in the memory 414.

While the present invention is illustrated, for example, with reference to the Module 450 being an application program in FIG. 25, as will be appreciated by those of skill in the art, other configurations may also be utilized while still benefiting from the teachings of the present invention. For example, the Module 450 may also be incorporated into the operating system 452, the I/O device drivers 458 or other such logical division of the data processing system 405. Thus, the present invention should not be construed as limited to the configuration of FIG. 25, which is intended to encompass any configuration capable of carrying out the operations described herein.

The I/O data port can be used to transfer information between the data processing system 405 or another computer system or a network (e.g., the Internet or Cloud) or to other devices controlled or directed by the processor 410. These components may be conventional components such as those used in many conventional data processing systems which may be configured in accordance with the present invention to operate as described herein.

For example, the data processing system 405 can be a computer program product with computer readable program code configured to provide a plurality of different predetermined operational modes.

While the present invention is illustrated, for example, with reference to particular divisions of programs, functions and memories, the present invention should not be construed as limited to such logical divisions. Thus, the present invention should not be construed as limited to the configuration of FIG. 25 but is intended to encompass any configuration capable of carrying out the operations described herein.

The operation and sequence of events can be controlled by at least one programmable logic controller.

The flowcharts and block diagrams of certain of the figures herein illustrate the architecture, functionality, and operation of possible implementations of olfactory test or training protocols according to the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved Embodiments of the invention allows for verification of the quality or concentration of a delivered odorant for evaluating olfactory function No known existing commercial test of olfactory function provides for verification of the quality or concentration of the delivered odorant. It is believed that this shortcoming, because decreases in olfactory function are biomarkers for debilitating neurodegenerative disease, confounds comparisons of repeated, longitudinal test results.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed:

1. A method of evaluating olfactory function, comprising:
   electronically estimating a user-specific odorant detection sensitivity threshold using at least one target stimulus odorant delivered to a nose of a user;
   flowably delivering a plurality of different target stimulus odorants to the nose of the user with defined concentrations of the different target stimulus odorants based, at least in part, on the estimated user-specific odorant detection sensitivity threshold; and
   evaluating olfactory function of the user based on the user's response to the delivered different target stimulus odorants.

2. The method of claim 1, wherein the estimating the user-specific odorant detection threshold sensitivity threshold comprises flowably delivering the at least one target stimulus odorant to the nose of the user in an ascending and/or descending staircase trial sequence and calculating a median or average of a concentration level associated with first and second positive identification concentration levels of different trials over time.

3. The method of claim 1, further comprising delivering an adapting odorant for a first duration and delivering one or more of the different target stimulus odorants concurrently with the adapting odorant and at an increased concentration relative to the adapting odorant and for a shorter duration than the adapting odorant to evaluate adaptation of the user.

4. The method of claim 1, wherein the different target stimulus odorants are flowably delivered to the nose of the user based on a nasal inhalation mask or nostril tube allowing one or more of: concurrent bilateral (birhinal) nostril delivery or independent single nostril (monorhinal) delivery.

5. The method of claim 1, further comprising delivering an adapting odorant for a first duration and delivering one or more of the different target stimulus odorants at different increasing onset intervals and shorter durations concurrently with the adapting odorant to evaluate adaptation of the user.

6. The method of claim 1, wherein the defined target stimulus odorants are flowably provided in calibrated concentrations (ppm or ppb) that are adjusted to compensate for environment variables so that each target stimulus odorant is presented to the user in a precise reliable concentration (ppm or ppb) and/or is calculated post-delivery to identify a precise and reliable concentration (ppm or ppb) delivered to the user to thereby allow for standardization in measurements across different users.

7. The method of claim 1, wherein the flowably delivering is carried out in defined sequences, and wherein the evaluating measures four olfactory functions: sensitivity, odor identification, odor discrimination and odor adaptation.

8. The method of claim 1, further comprising electronically obtaining responses of the user and electronically transmitting the responses to a remote database for one or more of storage, reporting and analysis.

9. The method of claim 7, further comprising calculating an olfactory index based on the measured four olfactory functions.

10. The method of claim 1, wherein the different target stimulus odorants that are flowably delivered to the user include a series of homologous aliphatic alcoholics or aldehydes, sharing a common functional group, but varying from three to eight carbon atoms in length to test pairwise discrimination ability.

11. The method of claim 1, wherein the defined concentrations are calibrated concentrations that are electronically adjusted according to local temperature, pressure and humidity conditions prior to, during or after the estimating and/or the flowably delivering.

12. The method of claim 1, wherein the defined concentrations are calibrated by providing fractional dilution values and saturation concentration for a respective target stimulus odorant at environmental local conditions, then converting the fractional dilution values to absolute values using the saturation concentration for the odorant.

13. The method of claim 1, wherein the defined concentration values are scaled concentration values calculated using the user-specific estimated sensitivity threshold.

14. The method of claim 1, wherein the flowably delivering of the different target stimulus odorants is carried out for: (i) discrimination testing of the user whereby the user is provided two different odorants to see if the user can detect whether they are different, (ii) adaptation testing whereby at least one adapting odorant is presented to the user with at least one of the target stimulus odorant and a response as to whether the target stimulus odorant is detected is obtained with or without an associated time of detection, and (iii) identification testing of the user whereby a response of the user to a correct identification of the target stimulus odorant delivered is measured.

15. The method of claim 1, wherein the flowably delivering of the different target stimulus odorants comprises:
providing the different target stimulus odorants in different odorant devices comprising sealed enclosed chambers in fluid communication with a fluid manifold;
providing at least one syringe of a carrier gas in fluid communication with the manifold;
flowing the carrier gas at a controlled flow rate from one of the at least one syringe through a first selected one of the sealed enclosed chambers to flow a respective associated target stimulus odorant in the enclosed chamber as an odorant vapor in the carrier gas into a flow path comprising the manifold then to a conduit attached to a nasal delivery device to deliver the target stimulus to the nose of the user.

16. The method of claim 15, further comprising purging the conduit, then flowing the carrier gas at a controlled flow rate from one of the at least one syringe through a second selected one of the sealed enclosed chambers to flow a respective associated target stimulus odorant as an odorant vapor in the carrier gas into a flow path comprising the manifold then to a conduit attached to the nasal delivery device, optionally a mask, for monorhinal or birhinal delivery.

17. The method of claim 15, wherein the at least one syringe is coupled to a three-way valve that selectively coupled the at least one syringe to either a clean air input or the fluid manifold.

18. The method of claim 15, further comprising electronically controlling the controlled flow rate of the carrier gas based on a target concentration value of a selected target stimulus odorant, a saturation concentration for the first selected odorant, and a target concentration relative to the saturation concentration.

19. The method of claim 15, further comprising adjusting the controlled flow rate from one of the at least one syringe through the first selected one of the sealed enclosed chambers based on local environmental conditions.

* * * * *

UNITED STATES PATENT AND TRADEMARK OFFICE
CERTIFICATE OF CORRECTION

| | | |
|---|---|---|
| PATENT NO. | : 11,986,310 B2 | Page 1 of 1 |
| APPLICATION NO. | : 16/648046 | |
| DATED | : May 21, 2024 | |
| INVENTOR(S) | : Smith et al. | |

It is certified that error appears in the above-identified patent and that said Letters Patent is hereby corrected as shown below:

In the Specification

Column 4, Line 21: Please correct "CH" to read --OI--

Signed and Sealed this
Seventh Day of January, 2025

Derrick Brent
*Acting Director of the United States Patent and Trademark Office*